US007612035B2

(12) United States Patent
Koo et al.

(10) Patent No.: US 7,612,035 B2
(45) Date of Patent: Nov. 3, 2009

(54) INHIBITION OF MITOGEN-ACTIVATED PROTEIN KINASE (MAPK) PATHWAY: A SELECTIVE THERAPEUTIC STRATEGY AGAINST MELANOMA

(75) Inventors: Han-Mo Koo, Kentwood, MI (US); Eunmi (Kay) Koo, legal representative, Kentwood, MI (US); George F. Vande Woude, Ada, MI (US); Nicholas S. Duesbery, Grand Rapids, MI (US)

(73) Assignee: Van Andel Research Institute, Grand Rapids, MI (US)

( * ) Notice: Subject to any disclaimer, the term of this patent is extended or adjusted under 35 U.S.C. 154(b) by 323 days.

(21) Appl. No.: 11/155,691

(22) Filed: Jun. 20, 2005

(65) Prior Publication Data

US 2005/0267012 A1 Dec. 1, 2005

Related U.S. Application Data

(62) Division of application No. 09/942,940, filed on Aug. 31, 2001, now abandoned.

(60) Provisional application No. 60/285,690, filed on Apr. 24, 2001, provisional application No. 60/229,290, filed on Sep. 1, 2000.

(51) Int. Cl.
*A61K 38/00* (2006.01)

(52) U.S. Cl. ......................... 514/2; 530/350; 435/252.3

(58) Field of Classification Search ..................... 512/2; 530/350; 435/252.3
See application file for complete search history.

(56) References Cited

U.S. PATENT DOCUMENTS

| | | | |
|---|---|---|---|
| 5,405,941 | A | 4/1995 | Johnson |
| 5,525,625 | A | 6/1996 | Bridges et al. |
| 5,591,631 | A | 1/1997 | Leppla et al. |
| 5,677,274 | A | 10/1997 | Leppla et al. |
| 5,958,721 | A | 9/1999 | Marshall et al. |
| 6,214,851 | B1 | 4/2001 | Duncia et al. |

FOREIGN PATENT DOCUMENTS

| | | | |
|---|---|---|---|
| GB | 2323845 | A | 7/1998 |
| WO | 92/19720 | A1 | 11/1992 |
| WO | 94/18332 | A2 | 8/1994 |
| WO | 94/23039 | A1 | 10/1994 |
| WO | 98/25598 | A2 | 6/1998 |
| WO | 99/01426 | A1 | 1/1999 |
| WO | 99/50439 | A2 | 10/1999 |
| WO | 00/37141 | A1 | 6/2000 |
| WO | 00/42002 | A1 | 7/2000 |
| WO | 00/42029 | A1 | 7/2000 |
| WO | 00/56706 | A1 | 9/2000 |
| WO | 00/68199 | A1 | 11/2000 |
| WO | 00/68201 | A1 | 11/2000 |
| WO | 02/076496 | A1 | 10/2002 |

OTHER PUBLICATIONS

Hsieh et al, 2007 (British J cancer, 97: 453-457).*
Bowie (Science, 1990, 257:1306-1310).*
Burgess et al ( J of Cell Bio. 111:2129-2138, 1990).*
Lazar et al (Molecular and Cellular Biology, 1988, 8:1247-1252).*
Kalechman et al. Int J Cancer, 86: 281-288.*
Adjei, Alex A., "The Role of Mitogen-Activated ERK-Kinase Inhibitors in Lung Cancer Therapy," Translational Medicine, Nov. 2005, pp. 221-223.
Milella, M. et al., "Beyond Single Pathway Inhibition: MEK Inhibitors as a Platform for the Development of Pharmacological Combinations with Synergistic Anti-Leukemic Effects," Current Pharmaceutical Design, 2005, pp. 2779-2795.
Cappuzzo, Frederico et al., "Emerging drugs for non-small cell lung cancer," Expert Opinion, 2003, pp. 179-192.
Sebolt-Leopold, Judith S., "MEK Inhibitors: A Therapeutic Approach to Targeting the Ras-MAP Kinase Pathway in Tumors," Current Pharmaceutical Design, 2004, pp. 1907-1914.
Arora, N., Site directed mutagenesis of histidine residues in anthrax toxin lethal factor binding domain reduces toxicity. Molecular and Cellular Biochemistry 177: 7-14 (1997).
Brossier F, et al., Role of Toxin Functional Domains in Anthrax Pathogenesis. Infection and Immunity 68 (No. 4): 1781-1786 (Apr. 2000).
Database Biosis Online Biosciences Information Service, Philadelphia, PA; Oct. 1999; Price, David T. et al: "Activation of extracellular signal-regulated kinase in human prostate cancer" (2 pages).
Database Biosis Online Biosciences Information Service, Philadelphia, PA; Nov. 16, 2000; Bonati, Antonio et al., "Selective Inhibition of MEK1 kinase downmodulates ERK activity and proliferation of AML blasts" (2 pages).
Duesbery N, et al., Anthrax lethal factor causes proteolytic inactivation of mitogen-activated protein kinase Journal of Applied Microbiology 87: 289-293 (1999).
Duesbery N, et al., CENP-E is an essential kinetochore motor in maturing oocytes and is masked during Mos- dependent, cell cycle arrest at metaphase II. Proc. Natl. Acad. Sci. 94: 9165-9170 (Aug. 1997).
Dunn F.B., Anthrax as a Cancer Drug? Journal of the National Cancer Institute 93 (22): 1680-1681 (Nov. 21, 2001).
Klimpel K, et al., Anthrax toxin lethal factor contains a zinc metalloprotease consensus sequence which is required for lethal toxin activity. Molecular Microbiology 13 (6): 1093-1100 (1994).
Koo H, et al., Enhanced Sensitivity to 1β-D-Arabinofuranosylcytosine and Topoisomerase II Inhibitors in Tumor Cell Lines Harboring Activated ras Oncogenes. Cancer Research 56: 5211-5216 (Nov. 15, 1996).

(Continued)

*Primary Examiner*—Larry R. Helms
*Assistant Examiner*—Minh-Tam Davis
(74) *Attorney, Agent, or Firm*—Price, Heneveld, Cooper, DeWitt & Litton, LLP

(57) ABSTRACT

Inhibitors of the MAPK pathway, including MEK-directed proteases and small molecule inhibitors, are cytotoxic to human melanoma cells in vitro and in vivo via apoptotic mechanisms. These compounds are used to kill melanoma cells and to treat subjects with melanoma, either alone or in combination with other therapeutic modalities.

9 Claims, 16 Drawing Sheets

OTHER PUBLICATIONS

Liu S, et al., Targeting of Tumor Cells by Surface Urokinase Plasminogen Activator-dependent Anthrax Toxin. The Journal of Biological Chemistry. 276 (21): 17976-17984 (May 25, 2001).

Menard A, et al., The cytotoxic activity of Bacillus anthracis lethal factor is inhibited by leukotriene A4 hydrolase and metallopeptidase inhibitors. Biochem J. 320: 687-691 (1996).

Oka H, et al. Constitutive Activation of Mitogen-activated Protein (MAP) Kinase in Human Renal Cell Carcinoma. Cancer Research 55: 4182-4187 (Sep. 15, 1995).

Pannifer A, et al., Crystal structure of the anthrax lethal factor. Nature 414: 229-233 (Nov. 8, 2001).

Pellizzari R, et al., Anthrax lethal factor cleaves MKK3 in macrophages and inhibits the LPS/IFNγ-induced release of NO and TNFα. FEBS Letters 462: 199-204 (1999).

Pugsley A., Bacterial toxins deliver the goods. Proc. Natl. Acad. Sci, 93: 8155-8156 (Aug. 1996).

Vitale G, et al., Susceptibility of mitogen-activated protein kinase kinase family members to proteolysis by anthrax lethal factor. Biochem J. 352: 739-745 (2000).

Weinstein J, et al., An Information-Intensive Approach to the Molecular Pharamcology of Cancer. Science 275: 343-349 (Jan. 17, 1997).

\* cited by examiner

Fig. 1
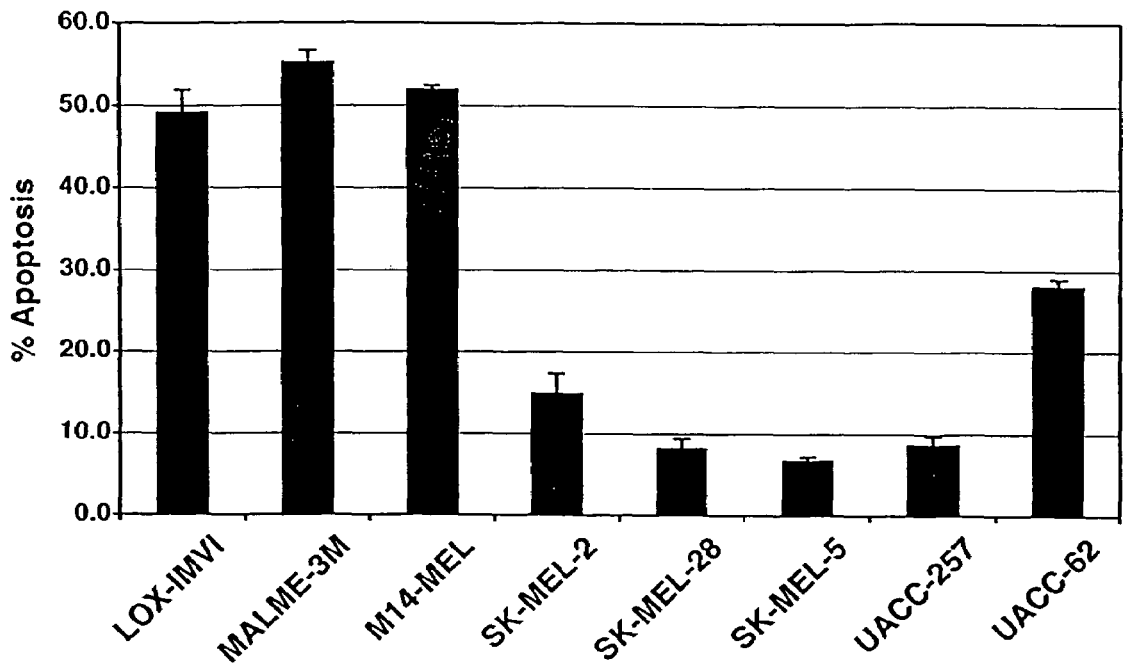
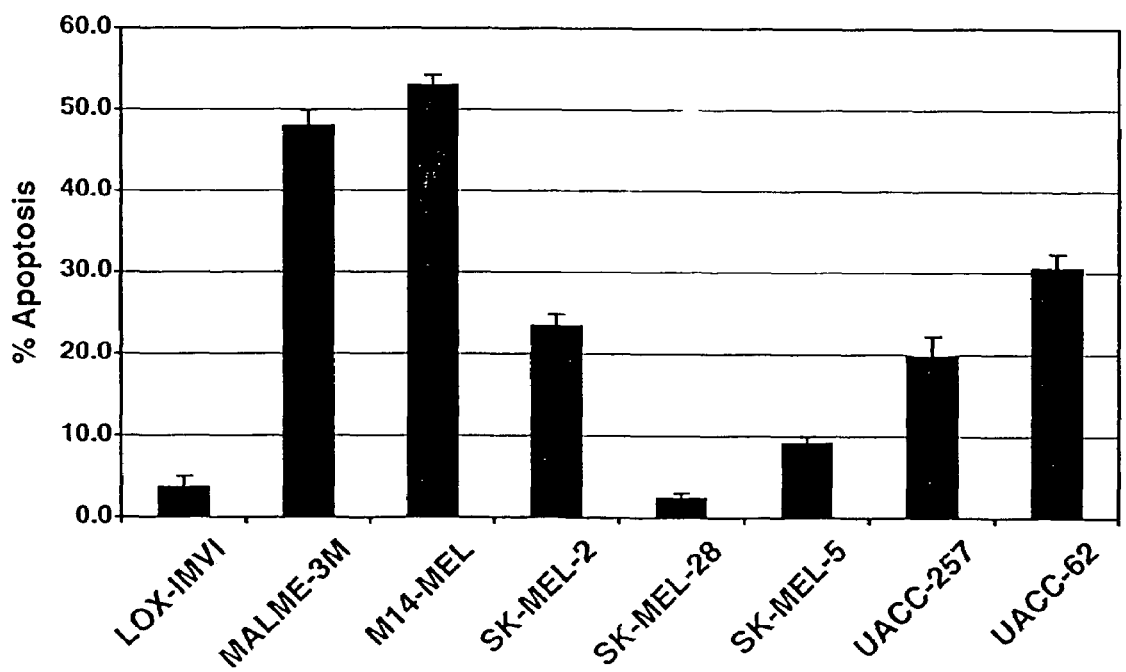
Fig. 2

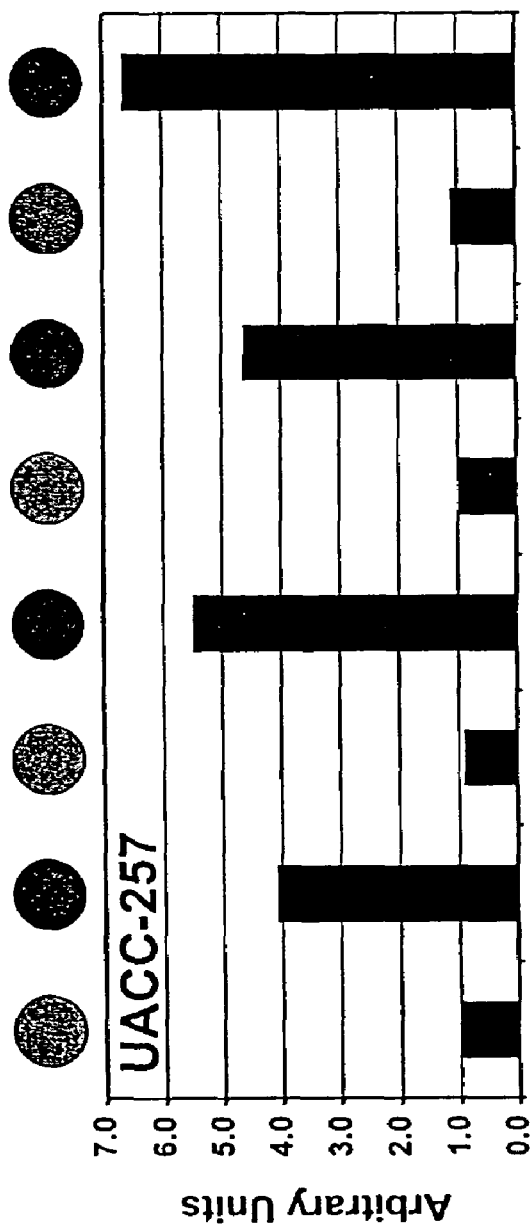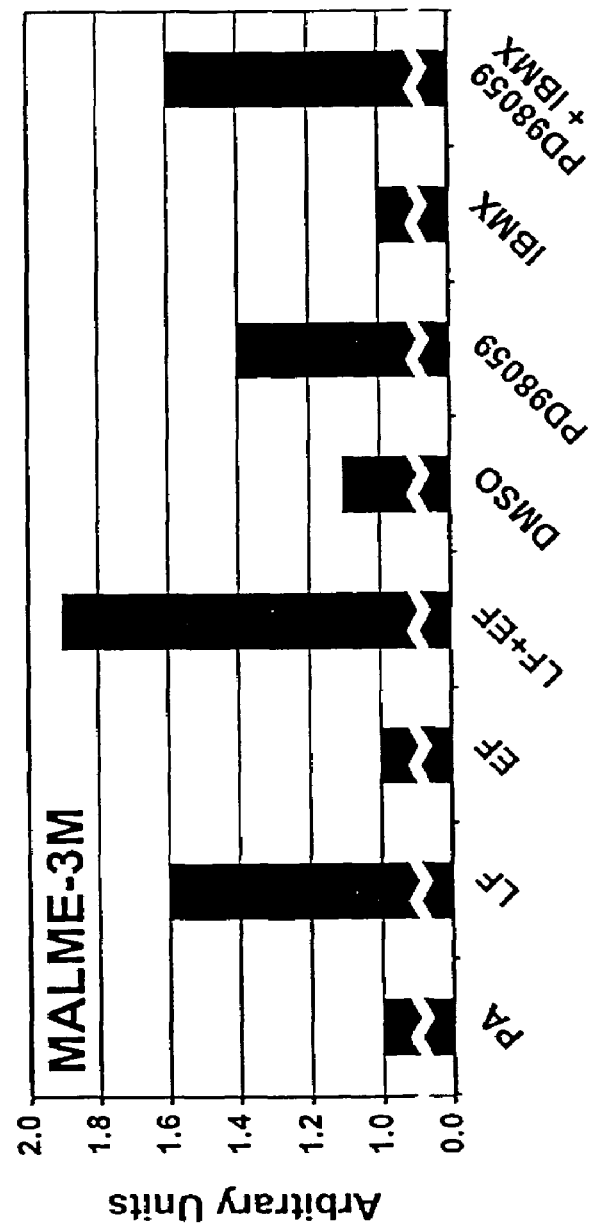

Fig. 17
M14-MEL
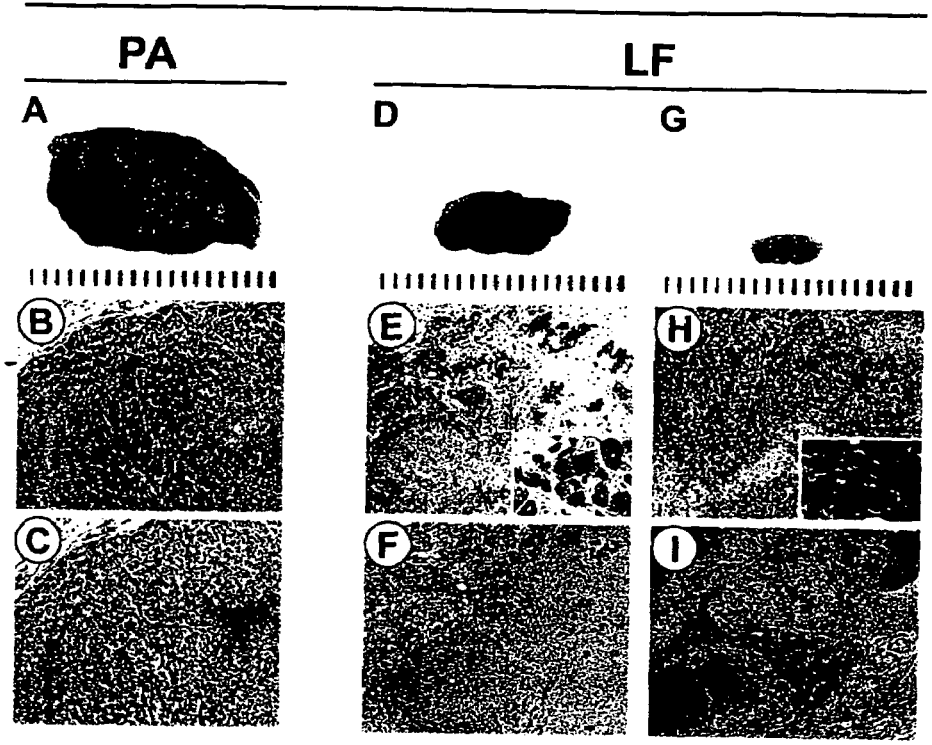
SK-MEL-28
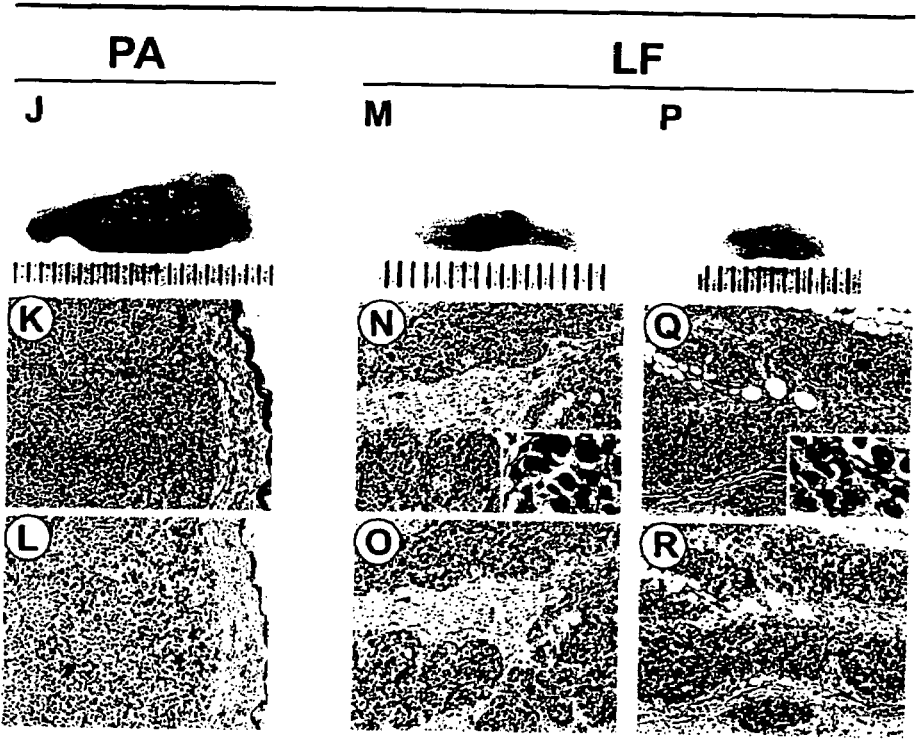

INHIBITION OF MITOGEN-ACTIVATED PROTEIN KINASE (MAPK) PATHWAY: A SELECTIVE THERAPEUTIC STRATEGY AGAINST MELANOMA

CROSS-REFERENCE TO RELATED APPLICATIONS

This application is a division of U.S. patent application Ser. No. 09/942,940 filed Aug. 31, 2001, now abandoned, entitled INHIBITION OF MITOGEN-ACTIVATED PROTEIN KINASE (MAPK) PATHWAY: A SELECTIVE THERAPEUTIC STRATEGY AGAINST MELANOMA, which claims priority to U.S. Provisional Patent Application No. 60/285,690 filed Apr. 24, 2001 and U.S. Provisional Patent Application No. 60/229,290 filed Sep. 1, 2000.

BACKGROUND OF THE INVENTION

1. Field of the Invention

The invention in the field of biochemistry and medicine relates to methods to kill melanoma cells and treat melanoma tumors in a selective manner using compositions that inhibit the mitogen-activated protein kinase (MAPK) pathway.

2. Description of the Background Art

The MAPK pathways are found in, and highly conserved among, all eukaryotes. These pathways play an integral role in the transduction of various extracellular signals into the nucleus. The best-characterized mammalian pathway, designated Raf-MEK1/2-ERK1/2, includes the MAPK enzymes also known as ERK1 and ERK2, which are phosphorylated and activated by the dual-specificity kinases that have been termed "MAPK/ERK kinases" (abbreviated variously as MAPKK1 and MAPKK2 or, as will be used herein, MEK1 and MEK2). The MEK enzymes are in turn phosphorylated and activated by the Raf kinases (Lewis, TS. et al., *Adv Canc Res*, 74:49-139 (1998)).

The MAPK pathway is involved in the regulation of cell growth, survival, and differentiation (Lewis et al., supra). Furthermore, activated MAPK and/or elevated level of MAPK expression have been detected in a variety of human tumors (Hoshino, R. et al., *Oncogene* 18:813-822 (1999); Salh, B et al., *Anticancer Res.* 19:741-48 (1999); Sivaraman, V S et al., *J. Clin. Invest.* 99:1478-483 (1997); Mandell, J W et al., *Am. J. Pathol.* 153:1411-23 (1998); Licato, L. L. et al. *Digestive Diseases and Sciences* 43, 1454-1464 (1998)) and may be associated with invasive, metastatic and angiogenic activities of tumor cells. Thus, inappropriate activation of the MAPK pathway is an essential feature common to many types of tumors. For this reason, participants in this signaling pathway, such as MEK, are potential targets for cancer therapy.

However, it has generally been observed that inhibitors of signal transduction, including of the MAPK pathway, are cytostatic in nature, merely arresting the growth of tumor cells but not killing them,. creating an expectation that non-traditional approaches would be required to develop such agents into clinical therapeutics.

The present inventors and their colleagues observed in the National Cancer Institute's Antineoplastic Drug Screen (NCI-ADS) database (Koo, H.-M. et al., *Canc Res* 56:5211-5216 (1996); Monks, A. et al. *J Natl Canc Inst* 83:757-766 (1991); Grever, M. R. et al., *Sem Oncol* 19:622-638 (1992)) that the lethal factor (LF) of *Bacillus anthracis*, a MEK-directed protease (Duesbery, N. S. et al., *Science* 280:734-737 (1998); Vitale, G. et al., *Biochem Biophys Res Comm* 248: 706-711-(1998)) and the small molecule pharmacological MEK inhibitor PD98059 (Dudley, D. T. et al., *Proc Nat'l Acad Sci USA* 92:7686-7689 (1995); Alessi, D. R. et al., *J Biol Chem* 270:27489-27494 (1995)) displayed enhanced growth inhibition specifically against melanoma lines among the many different tumor cell lines tested. Another small molecule MEK inhibitor, PD184352, has been described (Sebolt-Leopold, J S et al., *Nature Med.* 5: 810-816 (1999)).

The present invention is based on subsequent work wherein the inventors explored the mechanism by which inhibition of the MAPK signaling would selectively inhibit the growth of the human melanoma cells.

The incidence of malignant melanoma is increasing dramatically in all parts of the world (Parker, S. et al., *CA Cancer J Clin* 47:5-27 (1997)). The estimated lifetime risk for the population with light-colored skin is reaching 1 in 75 by the year 2000. Melanoma can be one of the most aggressive malignancies as the tumor readily metastasizes early in disease progression. Early detection and surgical intervention remain the mainstays of treatment for localized melanoma. Despite improved diagnosis and characterization, long-term survival from the advanced disease has not improved.

The present inventors' observation that inhibition of MAPK signaling specifically triggers an apoptotic response in human melanoma cells, but not in normal melanocytes or in other cell types, provides a novel, selective therapeutic strategy for systematic treatment of malignant melanomas.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present inventors found that sustained inhibition of MAPK signaling in human melanoma cells, preferably at least 72 hours in duration, evoked a selective cytotoxic response via apoptosis and results in killing of the entire cell population so treated. The results described herein serve as the basis of a novel, specific therapeutic strategy for melanoma based on inhibition of the MAPK pathway that leads to cytotoxicity and death of melanoma cells by apoptosis.

This invention provides a selective therapeutic approach to treat melanoma. According to the present approach, inhibition of MEK1/2 which are essential components of a MAPK (=ERK1/2) pathway, induces apoptosis selectively in melanoma cells, particularly in human melanoma cells, resulting in a cytotoxic rather than a cytostatic effect.

In one embodiment, a method of killing melanoma cells comprises contacting the cells for an effective time with an effective amount of an inhibitor of the MAPK pathway which induces apoptosis in the cells. Preferably the contacting is in vivo.

In another embodiment, a method of protecting against melanoma in a susceptible subject comprises administering to the subject that is (a) at risk for development of melanoma or (b) in the case of an already treated subject, at risk for recurrence of melanoma, an effective amount of a MAPK pathway inhibitor.

In another embodiment, a method of inducing an antitumor response in a mammal having melanoma comprises administering an effective amount of an inhibitor of the MAPK pathway to the mammal, which MAPK pathway inhibitor is cytotoxic to melanoma cells, thereby inducing an antitumor response that is (a) a partial antitumor response characterized by (i) at least a 50% decrease in the sum of the products of maximal perpendicular diameters of all measurable lesions;
(ii) no evidence of new lesions, and
(iii) no progression of any preexisting lesions, or
(b) a complete antitumor response characterized by the disappearance of all evidence of melanoma disease for at least one month.

In another embodiment, a method of inhibiting growth or recurrent growth of a melanoma tumor in a mammal having melanoma or at risk for melanoma growth or recurrence, comprises administering an effective amount of an inhibitor of the MAPK pathway to the mammal, thereby inducing a cytotoxic response leading to apoptosis of melanoma cells in the mammal, which inhibits the growth or recurrent growth of the melanoma tumor.

In the above embodiment, the MAPK pathway inhibitor is preferably an inhibitor of MEK (i.e., MEK1 and MEK2) such as *Bacillus anthracis* lethal factor (LF), a functional derivative thereof or another MEK-specific protease that results in the efficient induction of apoptosis in human melanoma cells.

In another embodiment, inhibition of the MAPK pathway is by a small molecule inhibitor, preferably PD98059 or U0126, which also results in the efficient induction of apoptosis in human melanoma cells.

In response to MEK inhibition, melanoma cells initially experience G1 cell cycle arrest. However, sustained inhibition of the pathway leads to efficient apoptosis. This differs from the response of most other cell types tested so far: these other cells remain arrested in G1, even after prolonged MEK inhibition, without signs of cell death. Thus, the effect on these other cell types is cytostatic rather than cytotoxic.

Apoptosis of melanoma cells by MEK inhibition coincides with a complete inhibition of the activation of MAPK1/2 (=ERK1/2), kinase enzymes "downstream" from MEK1/2.

MEK inhibition also stimulates melanoma cells to produce melanin, a phenotype associated with differentiated melanocytes and melanoma cells. Cyclic AMP (cAMP)-elevating agents are known to induce differentiation accompanied by melanin production in melanoma cells. While the cAMP-elevating agents, such as *Bacillus anthracis* edema factor (EF) and isobutylmethylxanthine (IBMX) synergize with MEK inhibitors in their effects on melanin production, EF or IBMX dominantly antagonize apoptosis induced by MEK inhibition.

In contrast to its effect on melanoma cells, MEK inhibition, is not cytotoxic to normal human melanocytes. While MEK inhibition completely blocks the activation of MAPK in normal melanocytes, and the cells are arrested in G1, apoptosis is not detected even after prolonged inhibition.

Long-term treatment of mixed cultures of melanoma cells and skin keratinocytes (in a. 1:1 ratio) with LF results in selective killing of the melanoma cells while the surviving keratinocytes remain reversibly arrested in G1.

The present invention is useful as a selective therapeutic strategy for the treatment of melanoma. The inhibition of MAPK pathway is cytotoxic (mediated by an apoptotic mechanism) only to melanoma cells whereas it is cytostatic (growth arrest) to most other cell types and normal melanocytes. Therefore, such a strategy provides a selective and systematic method to treat malignant melanoma.

An important advantage of this invention is the relative absence or mildness of side effects that accompany this systemic therapeutic strategy. This is because the inhibiting the MAPK pathway is cytostatic and therefore reversible in most cell types. Hence, minimal side-effects are expected and those unforeseen side-effects should reverse upon cessation of therapy.

The approach described herein may be combined with other treatment modalities to prevent initial appearance, or more importantly, prevent recurrence of melanoma.

The present invention therefore provides a method of killing melanoma cells comprising contacting the cells for an effective time with an effective amount of an inhibitor of the MAPK pathway which induces apoptosis in the cells. A preferred inhibitor is a MEK-directed protease, such as *Bacillus anthracis* lethal factor ("LF") or a functional derivative thereof.

The inhibitor may be an organic small molecule, such as PD98059, U0126 or PD184352.

In the above method, the contacting is preferably in vivo. The killing preferably results in measurable regression of melanoma tumor or attenuation of melanoma growth.

Also provided is a method of protecting against melanoma in a susceptible subject, comprising administering to the subject that is (a) at risk for development of melanoma or, (b) in the case of an already treated subject, at risk for recurrence of melanoma, an effective amount of a MAPK-inhibitor.

The invention is also directed to a method of inducing an antitumor response in a mammal having melanoma, comprising administering an effective amount of an inhibitor of the MAPK pathway to the mammal, which inhibitor is cytotoxic to melanoma cells, thereby inducing an antitumor response that is
(a) a partial antitumor response characterized by
(i) at least a 50% decrease in the sum of the products of maximal perpendicular diameters of all measurable lesions;
(ii) no evidence of new lesions, and
(iii) no progression of any preexisting lesions, or
(b) a complete antitumor response characterized by the disappearance of all evidence of melanoma disease for at least one month.

In the foregoing method, the inhibitor is preferably a MEK-directed protease such as LF or a functional derivative thereof. Alternatively, the inhibitor may be an organic small molecule, preferably PD98059, U0126 or PD184352.

In the above methods, the mammal is preferably a human.

This invention also provides a method of inhibiting growth or recurrent growth of a melanoma tumor in a mammal having melanoma or at risk for melanoma growth or recurrence, comprising administering an effective amount of an inhibitor of the MAPK pathway to the mammal, thereby inducing a cytotoxic response leading to apoptosis of melanoma cells in the mammal, which inhibits the growth or recurrent growth of the melanoma tumor. In the foregoing method, the inhibitor is preferably a MEK-directed protease such as LF or a functional derivative thereof. Alternatively, the inhibitor may be an organic small molecule, preferably PD98059, U0126 or PD184352.

BRIEF DESCRIPTION OF THE DRAWINGS

FIGS. 1 and 2 are graphs showing apoptosis induced by inhibition of the MAPK pathway in human melanoma cells. FIG. 1 shows induction of apoptosis by the MEK-directed protease LF. FIG. 2 shows induction of apoptosis by the small molecule MEK inhibitor PD98059. Apoptosis was quantified by staining DNA with DAPI followed by examining nuclear morphology of the stained cells. Standard deviations (of quadruplicate samples) are indicated

FIGS. 5A and 5B show the synergistic effect of EF and IBMX on melanogenesis induced by LF or PD98059 respectively in UACC-257 cells and MALME-3M cells. The melanin content was expressed in arbitrary units as a ratio compared to controls treated with PA alone (set as 1.0). The upper photographs (circles) correspond to the bars in the graphs below and depict a microplate well of UACC-257 cells (seeded at $4 \times 10^6$ cells/well). A single inoculation of DMSO (control) or 20 μM PD98059, a non-apoptotic concentration was used.

FIG. 10 is an immunoblot and FIGS. 11A-1D are cytograms showing responses of normal human primary melanocytes to inhibition of the MAPK pathway by LF. FIG. 10 shows an active phospho-MAPK immunoblot (top) and total MAPK immunoblot (bottom) of normal melanocytes (NHEM) or melanoma cells (MALME-3M) treated with PA alone ("PA") or LF plus PA ("LF") for the indicated durations. FIGS. 11A-11B show cell cycle profiles of NHEM cells treated with "PA" or "LF" for 96 hours. FIGS. 11C and 11C show profiles of MALME-3M cells treated in the same way for 72 hours. Percentage apoptosis, measured independently is indicated in the upper right corner of each panel.

FIGS. 12A-12D are cell cycle profiles and apoptosis (independently quantified and indicated in the upper right of each panel). The immunoblot (FIG. 13) shows active phospho-MAPK and total MAPK. The MEK inhibitor U0126 also did not induce apoptosis in normal melanocytes.

FIG. 17A-17R: show histological analysis ofthe M14-MEL (A-I) or SK-MEL-28 (J-R) xenograft tumors treated with PA or LF. For M14-MEL tumors treated with LF, both growing (D-F) and regressing (G-I) tumors were examined. (A, D, G, J, M, P). H&E and TUNEL staining and counterstaining were as in FIG. 14. Cross-sections of tumors (scale in mm); (B, E, H, K, N, Q). H&E staining of the tumor sections (insets in E, H, N, Q show melanin deposits in higher magnification); (ϵ, F, I, L, O, R) TUNEL staining of the adjacent sections - TUNEL-positive cells stained dark brown and nuclei (or DNA) stained light blue. TUNEL positivity found in the PA-treated M14-MEL tumor (C) was due to endogenous peroxidase activity of infiltrating leukocytes.

Figure 3:
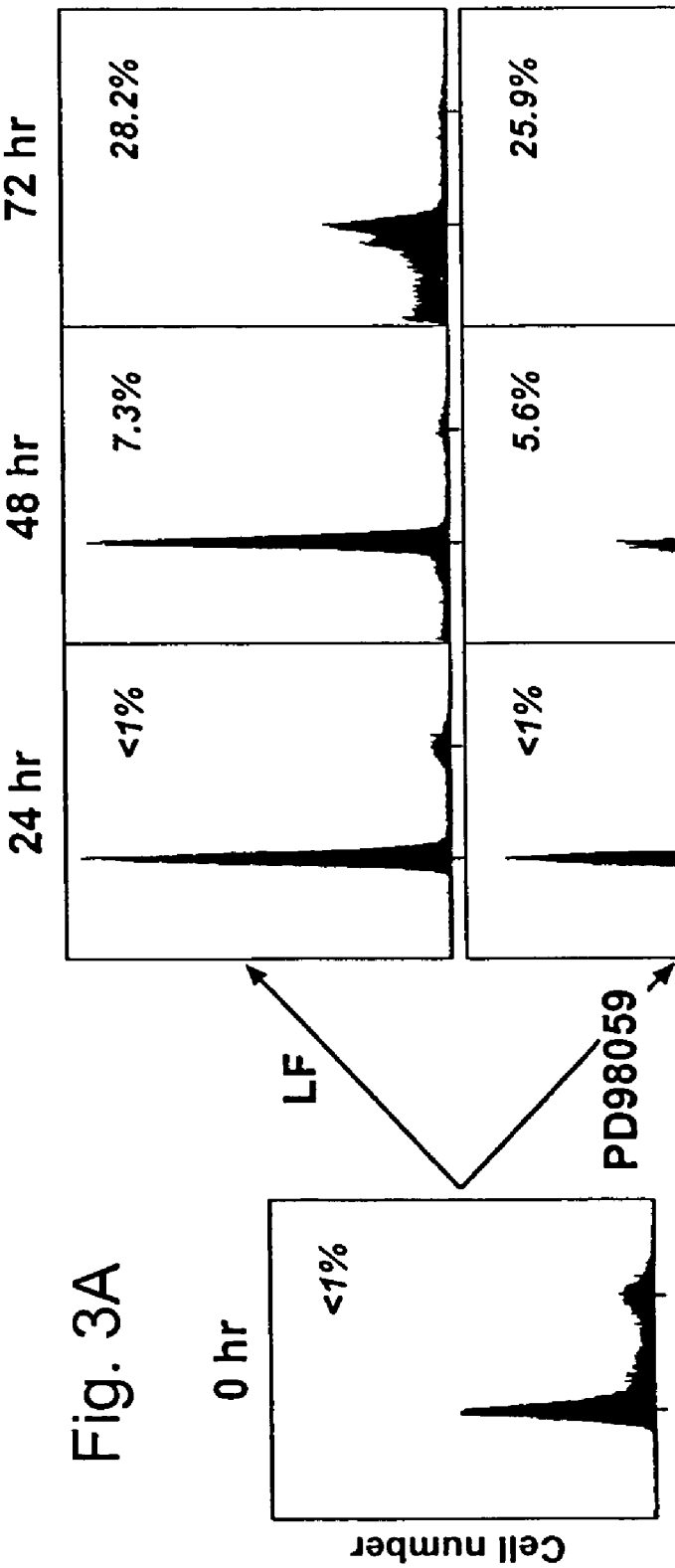
FIGS. 3A-3G show results of flow cytometric analysis of the cell cycle response of melanoma cells to sustained inhibition of the MAPK pathway. The progressive cell cycle response of MALME-3M cells to MAPK pathway inhibition by LF (FIGS. 3B-3D) or PD98059 (FIGS. 3E-3G) is shown. Percentage apoptosis indicated in each panel was quantified independently by staining a portion of the sample with DAPI followed by examination of nuclear morphology. Based on the control (0 hr), the 2C and 4C DNA content are indicated.

Treatment was either daily (○ and □) or at 2-day intervals (♦). For the daily treatment animal, a total of 4 doses was given; for the 2-day interval schedule, a total of 7 doses were given (arrowheads).

DESCRIPTION OF THE PREFERRED EMBODIMENTS

Hyperactivated or constitutively active kinases of the MAPK pathways are found in a variety of human cancers (Mandell et al., supra; Hoshino et al., supra; Sivaraman, et al., supra; Licato, L. L. et al., supra). These kinases offer potential therapeutic targets for treatment of the various forms of cancer. However, all known inhibitors of signal transduction including inhibitors of MAPK signaling have been found to be only cytostatic toward tumor cells. The present inventors have discovered that sustained inhibition of MAPK signaling by MEK inhibitors evokes a cytotoxic response via apoptosis that is selective for melanoma cells, particularly human melanoma. Induction of apoptosis is independent of the differentiation and/or growth arrest process induced by the MAPK signal inhibition. Furthermore, the cytotoxic response was highly specific to malignant melanoma cells as normal melanocytes did not undergo apoptosis in response to inhibition of the MAPK pathway. These results serve as the basis for the present invention that targets the MAPK pathway as a selectively cytotoxic melanoma-specific therapeutic strategy.

The term "sustained," as used herein in connection with inhibition of, or contact with, tumor cells or tumor tissue, is defined in terms of (a) duration of contact of the agent with the melanoma cells or (b) the number of repeated. cycles of treatment necessary for effective inhibition of tumor growth, stabilization or reduction of tumor size, or decrease in the number of tumor lesions. In a preferred embodiment, melanoma cells are subjected to an effective concentration of an inhibitor for at least 48 yours, more preferably 72 hours, even more preferably 96 hours to achieve the desired apoptosis and killing of a sufficient proportion of the cell population to have a discernible antitumor effect. In vivo, sustained contact is achieved by repeated administration of the inhibitor, preferably by injection, for the number of cycles necessary to result in the apoptotic death of a significant number of tumor cells that results in the desired pharmacological or clinical effect.

In one embodiment, the subject is given one weekly dose of the inhibitor, systemically or intratumorally. More preferably, the inhibitor is given twice per week, thrice per week or even daily. While the number of repeated doses to achieve the desired pharmacologic effect cannot always be predicted precisely in advance, those skilled in the art will know how to make these assessments, adjust doses and routes, change agents, etc., all as part of the routine clinical approach to treating subjects with melanoma.

Because of the "geometry" of cell death in a growing tumor in vivo, the cytotoxic compositions of the present invention may result in an "inside-out" killing of tumor cells after systemic (e.g., intravenous) or direct intratumoral administration. The mass of cells dying and dead within the tumor may remain for a period so that tumor shrinkage is not immediately detectable, even though the tumor is being successfully treated with the cytotoxic therapy of this invention. A better clinical end point may be the cessation of progressive growth of the tumor or a delay for a period of at least one month, preferably at least three months, more preferably at least six months.

Preferably, the treatment is continued until every detectable tumor cell is killed. Alternatively, other clinical endpoints are useful for gauging the success of the present compounds and methods, for example, significant shrinkage of the tumor mass. In any case, injections of the agent into the site formerly occupied by the tumor can be given intermittently even after the tumor has disappeared, for a period of days, weeks or months (see Examples).

Inhibitors of MEK

MEK-Directed Proteases

The term "MEK-directed protease activity" refers the proteolytic activity of a protease on MEK1 resulting in inactivation of MEK1. This term is intended to include protease activity on any member of the MEK family. The designation MEK refers to a family of protein kinases that are part of the MAPK pathway. Examples are MEK1, MEK2 and MEK3, etc.). These proteins share sequence similarity, particularly at the N-terminus. See, for example, Duesbery, NS et al., *CMLS Cell. Mol. Life Sci.* 55:1599-1609 (1999).

Thus, a MEK-directed protease refers to (1) a protease acting on members of the MEK protein family, (2) a protease that acts on conservative amino acid substitution variants or other conservatively modified variants thereof; and (3) a protease that acts on allelic or polymorphic variants, muteins and homologues in other species with greater than about 60%, preferably greater than about 70%, more preferably greater than about 80%, most preferably greater than about 90% sequence identity to MEK1, MEK2, MEK3, etc.

In one embodiment, MEK (i.e., MEK1 and MEK2) is inhibited by *Bacillus anthracis* lethal factor (LF), a MEK-specific protease. LF is cytotoxic toward V12H-ras-transformed NIH 3T3 cells and causes regression of MEK dependent tumor xenografts of these cells (Duesbery et al. *Proc. Natl. Acad. Sci. USA* 98: 4098-4094).

In another embodiment, the protease is a *Yersinia* protein, YopJ, and its homologues in other species and genera (avr-Rxv, Y4LO, AvrA), proteases that act on MEK1. LF, YopJ and their homologues, functional derivatives and mimetics are useful for inhibiting the MAPK pathway and having a cytotoxic action on melanoma cells and therefore, on melanoma tumors in vivo. See co-pending applications PCT US99/07126, filed Mar. 31, 1999, and having a priority date of Apr.

1, 1998; and U.S. Provisional Application Ser. No. 60/183,901, filed Feb. 22, 2000, hereby incorporated by reference in their entirety.

According to the present invention, the anti-melanoma cytotoxic protease inhibitor (or homologue or mimetic) exerts is proteolytic action by recognizing a specific amino acid sequence present in MEK1 or in any member of the MEK family. Thus, methods described herein as targeting MEK1 can be carried out similarly without undue experimentation and with the same expected effect using an inhibitor active on any other MEK family member.

While the present disclosure exemplifies use of *B. anthracis* LF as a MEK pathway inhibitor, it is to be understood that homologues of LF from other *Bacillus* species and mutants thereof that possess the characteristics disclosed herein are intended within the scope of this invention.

Also included is a "functional derivative" of LF, which is means an amino acid substitution variant, a "fragment," or a "chemical derivative" of LF, which terms are defined below. A functional derivative retains at least a portion of the relevant LF activity, that of proteolysis of MEK1 which permits its utility in accordance with the present invention.

With respect to the use of YopJ from *Yersinia pestis* or *Yersinia pseudotuberculosis*, it is to be understood that homologues of YopJ from other *Yersinia* species, and mutants thereof, that possess the characteristics disclosed herein are intended within the scope of this invention. Also included are "functional derivatives" of YopJ (as described above for LF).

A functional homologue must possess MEK-protease activity. In view of this functional requirement, use of homologous proteins to LF and YopJ from other bacterial species and genera, as well as from plant or animals sources, including proteins not yet discovered, fall within the scope of the invention if these proteins have sequence homology and the recited biochemical and biological activity.

It is within the skill in the art to obtain and express such a protein using DNA probes based on the sequence of LF or YopJ or *Salmonella*-derived or plant-derived homologues already characterized. Then, the protein's biochemical and biological activity can be tested readily using art-recognized methods such as those described herein, for example, a standard gel mobility shift assay for proteolysis of the substrate protein MEK1, or inhibition of MEK1-mediated phosphorylation of its natural substrate, MAPK, or of a model substrate. Finally, a biological assay of anti-melanoma activity such as those exemplified herein where apoptosis or other measures of cytotoxic action of the protein are assessed, will indicate whether the homologue has the requisite activity to qualify as a functional homologue.

A "variant" of the MEK-directed protease refers to a molecule substantially identical to either the full protein or to a fragment thereof in which one or more amino acid residues have been replaced (substitution variant) or which has one or several residues deleted (deletion variant) or added (addition variant). A "fragment" of the MEK-directed protease refers to any subset of the molecule, that is, a shorter polypeptide of the full length protein.

A preferred group of MEK-directed protease variants are those in which at least one amino acid residue and preferably, only one, has been substituted by different residue. For a detailed description of protein chemistry and structure, see Schulz, G E et al., *Principles of Protein Structure*, Springer-Verlag, New York, 1978, and Creighton, T. E., *Proteins: Structure and Molecular Properties*, W.H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups:

| | | |
|---|---|---|
| 1 | Small aliphatic, nonpolar or slightly polar residues | Ala, Ser, Thr (Pro, Gly); |
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The three amino acid residues in parentheses above have special roles in protein architecture. Gly, the only residue lacking a side chain, imparts flexibility to the chain. Pro, because of its unusual geometry, tightly constrains the chain. Cys can participate in disulfide bond formation which is important in protein folding.

More substantial changes in biochemical, functional (or immunological) properties are made by selecting substitutions that are less conservative, such as between, rather than within, the above five groups. Such changes will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (i) substitution of Gly and/or Pro by another amino acid or deletion or insertion of Gly or Pro; (ii) substitution of a hydrophilic residue, e.g., Ser or Thr, for (or by) a hydrophobic residue, e.g., Leu, Ile, Phe, Val or Ala; (iii) substitution of a Cys residue for (or by) any other residue; (iv) substitution of a residue having an electropositive side chain, e.g., Lys, Arg or His, for (or by) a residue having an electronegative charge, e.g., Glu or Asp; or (v) substitution of a residue having a bulky side chain, e.g., Phe, for (or by) a residue not having such a side chain, e.g., Gly.

Most acceptable deletions, insertions and substitutions according to the present invention are those that do not produce radical changes in the characteristics of the protein in terms of its proteolytic activity. However, when it is difficult to predict the exact effect of the substitution, deletion or insertion in advance of doing so, one skilled in the art will appreciate that the effect can be evaluated by routine screening assays such as those described here, without requiring undue experimentation.

Whereas shorter chain variants can be made by chemical synthesis, for the present invention, the preferred longer chain variants are typically made by site-specific mutagenesis of the nucleic acid encoding the polypeptide, expression of the variant nucleic acid in cell culture, and, optionally, purification of the polypeptide from the cell culture, for example, by immunoaffinity chromatography using specific antibody immobilized to a column (to absorb the variant by binding to at least one epitope).

The activity of a variant present in a cell lysate or a more highly purified preparation is screened in a suitable screening assay for the desired characteristic, preferably the proteolysis of MEK1. It is also possible to follow the immunological character of the protein molecule is assayed by alterations in binding to a given antibody, and may measured by competitive immunoassay. Biochemical or biological activity is screened in an appropriate assay, as described below.

A "mimetic" of a MEK-directed protease is an agent, generally a polypeptide or peptide molecule, that recognizes MEK, e.g., MEK1, as a substrate and cleaves MEK1 at the same site cleaved by full-length, native protease such as LF or YopJ. Thus, such mimetics include homologues, peptides, conservative substitution variants, as well as deletion variants that retain the protease active site and proteolytic action on MEK1. Such mimetics are tested using assays for protease activity, e.g., MEK1 mobility shift assays, MOS-induced activation of MAPK in oocytes and myelin basic protein (MBP) phosphorylation, as described below. In assessing a mimetic, LF is generally the positive control for protease activity. A mimetic has at least about 25% of the activity of this positive control, more preferably at least about 50-100% of the activity.

Also useful in the present methods are agents that potentiate or promote the above proteolytic activity may be used along with LF or YopJ, their homologues or mimetics to promote their anti-melanoma activity. A "potentiator" of the protease is an agent that activates (promotes, enhances, increases) the proteolytic activity and is identified by in vitro or in vivo assays of this activity or downstream activities in the MAPK pathway.

Samples that are treated with a candidate protease potentiator are compared to control samples that have not been treated with the test compound. This permits assessment of the presence and extent of activation of MEK1 protease activity. Control samples (untreated with test compounds) are assigned a relative protease activity value of 1. Activation is achieved when the measured protease activity value is about 1.5, more preferably 2.0 or greater. Potentiatiors can also be evaluated in a cellular assay, for example an assay for growth inhibition or apoptosis of human melanoma cells in culture as exemplified herein.

Fusion Proteins

The present invention utilizes a fusion protein comprising the MEK-directed protease (or homologue, functional derivative or mimetic) that is fused to another peptide or polypeptide that confers useful properties on the fusion protein.

One protein useful as a fusion partner is the domain of LF that binds to the protective antigen ("PA") of the anthrax toxin complex produced by Bacillus anthracis (Leppla, S H, "Anthrax Toxins," In: Handbook of Natural Toxins: Bacterial Toxins and Virulence Factors in Disease, Moss, J. et al., eds., Dekker, New York, 1995). For a recent review of anthrax toxins, see Duesbery, N S et al., CMLS Cell. Mol. Life Sci. 55:1599-1609 (1999). PA is one of three protein components of the "lethal" or "anthrax" toxin produced by B. anthracis. The 83 kDa PA binds to a cell surface receptor present on almost all vertebrate cells, and its C-terminus is necessary for this binding (Singh, Y et al., J. Biol. Chem. 264:19103-19107 (1989); Novak, J. et al., J. Biol. Chem. 267:17186-17193 (1992)). After binding, PA is specifically cleaved by a protease (e.g., furin, clostripain or trypsin), releasing a 20 kDa N-terminal PA fragment while a 63 kDa C-terminal PA fragment (PA63) remains bound. PA63, also referred to as "processed PA," contains the receptor binding site at its C-terminus. PA63 forms a heptameric membrane-inserted channel which mediates the entry of the two other protein components of the complex (LF, and Edema factor, EF) into the cytosol via the endosomal pathway (Gordon et al., Infect. Immun. 56:1066-1069 (1988); Milne et al., J. Biol. Chem. 269:20607-20612 (1994)).

To promote the uptake and processing of the MEK-directed protease (or homologue, derivative or mimetic), a fusion protein is made between the protease and the 250 amino acid PA-binding domain of LF. This will promote receptor binding and endosomal targeting of the fusion partner. As used herein, the term "PA" is a PA protein (or functional homologue or derivative) that has its receptor binding site intact and functional. U.S. Pat. Nos. 5,591,631 and 5,677,274 (incorporated by reference in their entirety) describe PA fusion proteins that target PA to particular cells, such as cancer cells, using, as fusion partners, ligands for receptors on the targeted cells. In contrast, the present invention exploits the receptor-binding properties of PA by creating fusion proteins between the MEK-directed protease and the PA-binding domain of LF. The LF domain can be fused at the N- or C-terminus of the protease. The full length MEK-directed protease is not required in this fusion protein as long as the domain(s) responsible for the protease activity is (are) present. Such fusion proteins have the advantage of facilitating the uptake of the proteolytic polypeptide into the endosomal compartment and ultimately into the cytoplasm of the cell being targeted.

Chemical Modification of the Protein

A "chemical derivative" of a MEK-directed protease contains additional chemical moieties not normally a part of the protein. Covalent modifications of the protein are included within the scope of this invention. Such modifications may be introduced into the molecule by reacting targeted amino acid residues with an organic derivatizing agent that is capable of reacting with selected side chains or terminal residues. Such chemically modified and derivatized moieties may improve the protein's solubility, absorption, biological half life, and the like. These changes may eliminate or attenuate undesirable side effects of the protein in vivo. Moieties capable of mediating such effects are disclosed, for example, in Remington's Pharmaceutical Sciences, Mack Publishing Company, Easton Pa. (Gennaro 18th ed. 1990).

Preparation of Recombinant MEK-Directed Protease (and MEK1) Proteins

As described herein, native or recombinant MEK-directed protease proteins, their homologues and mimetics are used in the methods of the invention. MEK1, the target of proteolytic activity, may also be provided in native or recombinant form for testing. Recombinant proteins may be particularly convenient for biochemical assays. MEK-directed protease homologues and functional derivatives such as substitution variants and fusion proteins may be prepared recombinantly for evaluation of their mimetic activity and therapeutic activity. Recombinant proteins are prepared by conventional means which are generally described below along with methods for biochemical isolation and purification of the proteins from natural sources.

General recombinant DNA methods

Basic texts disclosing general methods of molecular biology, all of which are incorporated by reference, include: Sambrook, J. et al., Molecular Cloning: A Laboratory Manual, 2nd Edition, Cold Spring Harbor Press, Cold Spring Harbor, N.Y., 1989; Ausubel, F. M. et al. Current Protocols in Molecular Biology, Vol. 2, Wiley-Interscience, New York, (current edition); Kriegler, Gene Transfer and Expression: A Laboratory Manual (1990); Glover, D. M., ed, DNA Cloning: A Practical Approach, vol. I & II, IRL Press, 1985; Albers, B. et al., Molecular Biology of the Cell, 2nd Ed., Garland Publishing, Inc., New York, N.Y. (1989); Watson, J. D. et al., Recombinant DNA, $2^{nd}$ Ed., Scientific American Books, New York, 1992; and Old, RW et al., Principles of Gene Manipulation: An Introduction to Genetic Engineering, $2^{nd}$ Ed., University of California Press, Berkeley, Calif. (1981).

Unless otherwise indicated, a particular nucleic acid sequence additionally encompasses conservative substitution variants thereof (e.g., degenerate codon substitutions) and a complementary sequence. The term "nucleic acid" is intended to include a gene, cDNA, mRNA, an oligonucleotide (any polynucleotide). Sizes of nucleic acids are stated either as kilobases (kb) or base pairs (bp). These are estimates derived from agarose electrophoresis or polyacrylamide gel electrophoresis (PAGE), from sequences of nucleic acids which are determined by the user or published. Protein sizes are stated as molecular mass in kilodaltons (kDa) or as length (number of amino acid residues). Proteins sizes are estimated from PAGE, from sequencing, from presumptive amino acid sequences based on nucleic acid sequence, or from published amino acid sequences.

Oligonucleotides that are not commercially available may be chemically synthesized (*Oligonucleotide Synthesis*, N. Gait, ed., Current Edition), for example, according to the solid phase phosphoramidite triester method (Beaucage et al., *Tetrahedron Lett.* 22:1859-1862 (1981)) using an automated synthesizer (Van Devanter et. al., *Nucleic Acids Res.* 12:6159-6168 (1984)). Oligonucleotides are purified by native acrylamide gel electrophoresis or by anion-exchange HPLC (Pearson et al., *J. Chromatog.* 255:137-149 (1983)). The sequence of a cloned gene or a synthetic oligonucleotide can be verified using the chain termination method for sequencing double-stranded templates (Wallace et al., *Gene* 16:21-26 (1981).

Cloning of nucleic acids encoding MEK-1 proteases and other proteins

In general, a nucleic acid encoding a MEK1 protease, PA, or a homologous nucleic acid is cloned starting from cDNA or genomic DNA libraries or is isolated by polymerase chain reaction (PCR) amplification techniques using oligonucleotide primers. For example, LF is isolated from *B. anthracis* and YopJ is typically isolated from *Y. pestis* DNA (genomic or cDNA) libraries. Genes for MEK1 can be cloned from mammalian libraries, preferably human libraries. For example, MEK1 sequences can be isolated from sarcoma libraries from cells with an activated MAPK pathway. PA can be cloned from a *B. anthracis* DNA library.

Amplification techniques using primers may also be employed to amplify and isolate PA, and MEK1 from DNA or RNA (U.S. Pat. Nos. 4,683,195 and 4,683,202; *PCR Protocols: A Guide to Methods and Applications* (Innis et al., eds, 1990)). PCR and ligase chain reaction (LCR) methods can be used to amplify a nucleic acid sequences directly from mRNA, cDNA or genomic DNA. Degenerate oligonucleotides are routinely designed to amplify homologues.

Small Molecule Inhibitors of MEK

Also intended within the scope of this invention are small organic molecules that act as inhibitors of MEK. As used herein, "small molecules" are organic chemical entities that are not biological macromolecules such as proteins or peptides. The small molecule inhibitors of MEK generally have a molecular mass of less than about 2000 D, preferably less than about 1000 D, more preferably less than about 500 D.

In a preferred embodiment, inhibition of MEK by the small molecule inhibitor PD98059 results in the efficient induction of apoptosis in cells of a human melanoma cell line.

Other small molecule inhibitors of the MAPK pathway are known to be, or are expected to be, cytotoxic to melanoma cells. These include the MEK inhibitors PD184352 (Parke-Davis) (Sebolt-Leopold et al., supra) and U0126 (DuPont) (Favata, M et al., *J. Biol. Chem.* 273:18623-18632 (1998)), the p38 kinase inhibitor SB 203580 (Schering-Plough) (Cuenda, A et al., *FEBS Lett.* 364:229-233 (1995)), and the like.

Pharmaceutical Compositions, Their Formulation and Use

A pharmaceutical composition according to this invention comprises the MEK-directed protease (or functional derivative or mimetic) or the small molecule MEK inhibitor, in a formulation that, as such, is known in the art.

Pharmaceutical compositions within the scope of this invention include all compositions wherein the MEK-directed protease or other small molecule MEK inhibitor is contained in an amount effective to achieve its intended purpose. While individual needs vary, determination of optimal ranges of effective amounts of each component is within the skill of the art. Typical dosages comprise 0.1 to 100 mg/kg/body wt, though more preferred dosages are described for certain particular uses, below.

In addition to the pharmacologically active protein or small molecule, the pharmaceutical compositions may contain suitable pharmaceutically acceptable carriers comprising excipients and auxiliaries which facilitate processing of the active compounds into preparations which can be used pharmaceutically as is well known in the art. Suitable solutions for administration by injection or orally, may contain from about 0.01 to 99 percent, active compound(s) together with the excipient.

The pharmaceutical preparations of the present invention are manufactured in a manner which is known, for example, by means of conventional mixing, granulating, dissolving, or lyophilizing processes. Suitable excipients may include fillers binders, disintegrating agents, auxiliaries and stabilizers, all of which are known in the art. Suitable formulations for parenteral administration include aqueous solutions of the proteins in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension.

The compositions may be in the form of a lyophilized particulate material, a sterile or aseptically produced solution, a tablet, an ampule, etc. Vehicles, such as water (preferably buffered to a physiologically acceptable pH, as for example, in phosphate buffered saline) or other inert solid or liquid material such as normal saline or various buffers may be present. The particular vehicle is not critical, and those skilled in the art will know which vehicle to use for any particular utility described herein.

In general terms, a pharmaceutical composition is prepared by mixing, dissolving, binding or otherwise combining the polymer or polymeric conjugate of this invention with one or more water-insoluble or water-soluble aqueous or non-aqueous vehicles. If necessary, another suitable additive or adjuvant is included. It is imperative that the vehicle, carrier or excipient, as well as the conditions for formulating the composition are such that do not adversely affect the biological or pharmaceutical activity of the protein, peptide or small molecule.

Subjects, Treatments Modes and Routes of Administration

The preferred animal subject of the present invention is a mammal. The invention is particularly useful in the treatment of human subjects. By the term "treating" is intended the administering to subjects of a pharmaceutical composition comprising a MEK inhibitor (whether a protease or a small molecule inhibitor). Treating includes administering the agent to subjects at risk for developing melanoma prior to evidence of clinical disease, as well as subjects diagnosed with melanoma who have not yet been treated or who have been treated by other means, e.g., surgery, conventional chemotherapy, and in whom tumor burden has been reduced even to the level of not being detectable. Thus, due to the melanoma-directed cytotoxic effects of the present methods, this invention is useful in preventing or inhibiting melanoma primary growth, recurrent growth or metastatic growth.

The pharmaceutical compositions of the present invention wherein the MEK-directed protease or inhibitor is combined with pharmaceutically acceptable excipient or carrier, may be administered by any means that achieve their intended purpose. Amounts and regimens for the administration of can be determined readily by those with ordinary skill in the clinical art of treating any of the particular diseases. Preferred amounts are described below.

In general, the present methods include administration by parenteral routes, including subcutaneous (s.c.) intravenous (i.v.), intramuscular, intraperitoneal, intrathecal, transdermal, topical or inhalation routes. A preferred route is by direct intratumoral injection. Alternatively, or concurrently, administration may be by the oral route. The dosage administered will be dependent upon the age, health, and weight of the recipient, kind of concurrent treatment, if any, frequency of treatment, and the nature of the effect desired.

In one treatment approach, the compounds and methods are applied in conjunction with surgery. Thus, an effective amount of the MEK protease or small molecule MEK inhibitor is applied directly to the site of surgical removal of a melanoma mass (whether primary or metastatic). This can be done by injection or "topical" application in an open surgical site or by injection after closure.

In a preferred embodiment, the specified amount of a MEK protease or inhibitor, preferably about 2-100 µg, is added to about 700 ml of human plasma that is diluted 1:1 with heparinized saline solution at room temperature. Human IgG in a concentration of 500 µg/dl (in the 700 ml total volume) may also be used. The solutions are allowed to stand for about 1 hour at room temperature. The solution container may then be attached directly to an iv infusion line and administered to the subject at a preferred rate of about 20 ml/min.

In another embodiment, the pharmaceutical composition is directly infused i.v. into a subject. The appropriate amount, preferably about 2-100 µg, is added to about 250 ml of heparinized saline solution and infused iv into patients at a rate of about 20 ml/min.

In the present method, the composition can be given one time but generally is administered six to twelve times (or even more, as is within the skill of the art to determine empirically). The treatments can be performed daily but are generally carried out every two to three days or as infrequently as once a week, depending on the beneficial and any toxic effects observed in the subject.

The pharmaceutical formulation for systemic administration according to the invention may be formulated for enteral, parenteral or topical administration, and all three types of formulation may be used simultaneously to achieve systemic administration of the active ingredient.

For lung instillation, aerosolized solutions are used. In a sprayable aerosol preparations, the active protein or small molecule agent may be in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the protein of the invention.

For topical application, the therapeutic compounds of the present invention may be incorporated into topically applied vehicles such as salves or ointments, as a means for administering the active ingredient directly to the affected area. Scarification methods, known from studies of vaccination, can also be used. The carrier for the active agent may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Examples of preferred vehicles for non-sprayable topical preparations include ointment bases, e.g., polyethylene glycol-1000 (PEG-1000); conventional creams such as HEB cream; gels; as well as petroleum jelly and the like.

Other pharmaceutically acceptable carriers according to the present invention are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension.

The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

In Vivo Study of MEK-Directed Proteases and Inhibitors
Antitumor Effects of MEK Pathway Inhibitors in Animal Models of Human Tumors The MEK inhibitory agents are tested for therapeutic efficacy in well established rodent models which are considered to be representative of a human tumor. The overall approach is described in detail in 1. Geran, R. I. et al., "Protocols for Screening Chemical Agents and Natural Products Against Animal Tumors and Other Biological Systems (Third Edition)", *Canc. Chemother. Reports*, Part 3, 3:1-112, and
2. Plowman, J. et al., In: B. Teicher, ed., Anticancer Drug Development Guide: Preclinical Screening, Clinical Trials and Approval, Part II: In Vivo Methods, Chapter 6, "Human Tumor Xenograft Models in NCI Drug Development," Humana Press Inc., Totowa, N.J., 1997.

Both these references are hereby incorporated by reference in their entirety.

I. General Test Evaluation Procedures
  A. Calculation of Mean Survival Time

Mean survival time is calculated according to the following formula:

$$\text{Mean survival time(days)} = \frac{\Sigma S + AS_{(A-1)} - (B+1)NT}{S_{(A-1)} - NT}$$

Definitions:

Day: Day on which deaths are no longer considered due to drug toxicity. Example: with treatment starting on Day 1 for survival systems (such as B16):

Day A: Day 6.

Day B: Day beyond which control group survivors are considered "no-takes." Example: with treatment starting on Day 1. For B16, Day B is to be established.

$\Sigma S$: If there are "no-takes" in the treated group, $\Sigma S$ is the sum from Day A through Day B. If there are no "no-takes" in the treated group, $\Sigma S$ is the sum of daily survivors from Day A onward.

$S_{(A-1)}$: Number of survivors at the end of Day (A−1).

Example: $S_{(A-1)}$=number of survivors on Day 5.

NT: Number of "no-takes" according to the criteria given in Protocols 7.300 and 11.103.

B. T/C Computed for all treated groups

T/C is the ratio (expressed as a percent) of the mean survival time of the treated group divided by the mean survival time of the control group. Treated group animals surviving beyond Day B, according to the chart below, are eliminated from calculations:

| No. of survivors in treated group beyond Day B | Percent of "no-takes" in control group | Conclusion |
|---|---|---|
| 1 | Any percent | "no-take" |
| 2 | <10 | drug inhibition |
| 2 | ≧10 | "no-takes" |
| ≧3 | <15 | drug inhibitions |
| ≧3 | ≧15 | "no-takes" |

Positive control compounds are not considered to have "no-takes" regardless of the number of "no-takes" in the control group. Thus, all survivors on Day B are used in the calculation of T/C for the positive control. Surviving animals are evaluated and recorded on the day of evaluation as "cures" or "no-takes."

Calculation of Median Survival Time

Median Survival Time is defined as the median day of death for a test or control group. if deaths are arranged in chronological order of occurrence (assigning to survivors, on the final day of observation, a "day of death" equal to that day), the median day of death is a day selected so that one half of the animals died earlier and the other half died later or survived. If the total number of animals is odd, the median day of death is the day that the middle animal in the chronological arrangement died. If the total number of animals is even, the median is the arithmetical mean of the two middle values. Median survival time is computed on the basis of the entire population and there are no deletion of early deaths or survivors, with the following exception:

C. Computation of Median Survival Time From Survivors

If the total number of animals including survivors (N) is even, the median survival time (days) (X+Y)/2, where X is the earlier day when the number of survivors is ≦N/2, and Y is the earliest day when the number of survivors ≦(N/2)−1. If N is odd, the median survival time (days) is X.

D. Computation of Median Survival Time From Mortality Distribution

If the total number of animals including survivors (N) is even, the median survival time (days) (X+Y)/2, where X is the earliest day when the cumulative number of deaths is ≧N/2, and Y is the earliest day when the cumulative number of deaths is ≧(N/2)+1. If N is odd, the median survival time (days) is X.

Cures and "No-Takes": "Cures" and "no-takes" in systems evaluated by median survival time are based upon the day of evaluation. On the day of evaluation any survivor not considered a "no-take" is recorded as a "cure." Survivors on day of evaluation are recorded as "cures" or "no-takes," but not eliminated from the calculation of the median survival time.

E. Calculation of Approximate Tumor Weight From Measurement of Tumor Diameters with Vernier Calipers The use of diameter measurements (with vernier calipers) for estimating treatment effectiveness on local tumor size permits retention of the animals for lifespan observations. When the tumor is implanted sc, tumor weight is estimated from tumor diameter measurements as follows. The resultant local tumor is considered a prolate ellipsoid with one long axis and two short axes. The two short axes are assumed to be equal. The longest diameter (length) and the shortest diameter (width) are measured with vernier calipers. Assuming specific gravity of ~1.0, and $\pi \approx 3$, the mass (in mg) is calculated by multiplying the length of the tumor by the width squared and dividing the product by two. Thus, $$\text{Tumor weight(mg)} = \frac{\text{length(mm)} \times (\text{width[mm]})^2}{2} \text{ or } (L \times W^2)/2$$

The reporting of tumor weights calculated in this way is acceptable inasmuch as the assumptions result in as much accuracy as the experimental method warrants.

F. Calculation of Tumor Diameters

The effects of a drug on the local tumor diameter may be reported directly as tumor diameters without conversion to tumor weight. To assess tumor inhibition by comparing the tumor diameters of treated animals with the tumor diameters of control animals, the three diameters of a tumor are averaged (the long axis and the two short axes). A tumor diameter T/C of 75% or less indicates activity and a T/C of 75% is approximately equivalent to a tumor weight T/C of 42%.

G. Calculation of Mean Tumor Weight From Individual Excised Tumors

The mean tumor weight is defined as the sum of the weights of individual excised tumors divided by the number of tumors. This calculation is modified according to the rules listed below regarding "no-takes." Small tumors weighing 39 mg or less in control mice are regarded as "no-takes" and eliminated from the computations. In treated groups, such tumors are defined as "no-takes" or as true drug inhibitions according to the rules shown in the following Table.

Positive control compounds are not considered to have "no-takes" regardless of the number of "no-takes" in the control group. Thus, the tumor weights of all surviving animals are used in the calculation of T/C for the positive control. T/C are computed for all treated groups having more than 65% survivors. The T/C is the ratio (expressed as a percent) of the mean tumor weight for treated animals divided by the mean tumor weight for control animals. SDs of the mean control tumor weight are-computed the factors in a table designed to estimate SD using the

| Percent of small tumors in treated group | Percent of "no-takes" in control group | Action |
| --- | --- | --- |
| ≦17 | Any percent | no-take; not used in calculations |
| 18-39 | <10 | drug inhibition; use in calculations |
|  | ≧10 | no-takes; not used in calculations |
| ≧40 | <15 | drug inhibition; use in calculations |
|  | ≧15 | Code all nontoxic tests "33" | estimating factor for SD given the range (difference between highest and lowest observation). Biometrik Tables for Statisticians (Pearson E S, and Hartley H G, eds.) Cambridge Press, vol. 1, table 22, p. 165.

Melanotic Melanoma B16 in C57BL/6 Mice
Summary:
Tumor homogenate is implanted ip or s.c. in $BDF_1$ mice. Treatment begins 24 hours after either ip or s.c. implant or is delayed until an s.c. tumor of specified size (usually approximately 400 mg) can be palpated. Results expressed as a percentage of control survival time. The test compound is administered ip, and the parameter is mean survival time. Origin of tumor line: arose spontaneously in 1954 on the skin at the base of the ear in a C57BL/6 mouse. *Handbook on Genetically Standardized Jax Mice*. Roscoe B. Jackson Memorial Laboratory, Bar Harbor, Me., 1962. See also *Ann NY Acad Sci* 100, *Parts 1 and 2*, 1963.

Animals
Propagation: C57BL/6 mice.
Testing: C57BL/6 or $BDF_1$ (C57BL16 x DBA/2) mice.
Weight: Within a 3-g weight range, with minimum 18 g for males, 17 g for females.
Sex: One sex used for all test and control groups in one experiment.
Experiment Size: Ten animals per test group. For control groups, the number varies according to the number of test groups.
Tumor Transfer
Propagation: Implant fragment s.c. by trochar or 12-gauge needle or tumor homogenate (see below) every 10-14 days into axillary region with puncture in inguinal region.
Testing: Excise s.c. tumor on Day 10-14.
Homogenate: Mix 1 g or tumor with 10 ml of cold balanced salt solution and homogenize, and implant 0.5 ml of this tumor homogenate ip or sc.
Fragment: A 25-mg fragment may be implanted sc.
Testing Schedule
Day 0: Implant tumor. Prepare materials. Run positive control in every odd-numbered experiment. Record survivors daily.
Day 1: Weigh and randomize animals. Begin treatment with therapeutic composition. Typically, mice receive the test compound in 0.5 ml saline. Controls receive saline alone. The treatment is given as one dose per week. Any surviving mice are sacrificed 8 weeks of therapy.
Day 5: Weigh animals and record.
Day 60: Kill all survivors and evaluate experiment.
Quality Control
Acceptable control survival time is 14-22 days. Positive control compound is 5-fluorouracil: single dose is 200 mg/kg/injection, intermittent dose is 60 mg/kg/injection, and chronic dose is 20 mg/kg/injection. T/C lower limit for positive control compound is ≧135%. Check control deaths, no takes, etc.

Evaluation
Compute mean animal weight on Days 1 and 5, and at the completion of testing compute T/C for all test groups with >65% survivors on Day 5. A T/C value ≦85% indicates a toxic test. An initial T/C≧125% is considered necessary to demonstrate activity. A reproduced T/C≧125% is considered worthy of further study. For confirmed activity a therapeutic composition should have two multi-dose assays that produce a T/C≧125%.

Metastasis after IV Injection of Tumor Cells
$10^5$ B 16 melanoma cells in 0.3 ml saline are injected intravenously to C57BL/6 mice. The mice are then treated intravenously with the test compound in 0.5 ml saline. Controls receive saline alone. The treatment is given as one dose per week. Mice sacrificed after 4 weeks of therapy, the lungs are removed and metastases are enumerated. The following are considered to be significant effects:

|  | Parameter | % of Control Response |
| --- | --- | --- |
| B16 | Mean or median survival time | >130% |
| B16 metastasis | Median number of metastases | <70% |

2. Human Tumor Xenograft Models

The preclinical discovery and development of anticancer drugs as implemented by the National Cancer Institute (NCI) consists of a series of test procedures, data review, and decision steps (Grever, M R, *Semin Oncol.*, 19:622-638 (1992)). Test procedures are designed to provide comparative quantitative data, which in turn, permit selection of the best candidate agents from a given chemical or biological class. Below, we describe human tumor xenograft systems, emphasizing melanomas, that are currently employed in preclinical drug development.

Since 1975, the NCI approach to drug discovery involved prescreening of compounds in the i.p.-implanted murine P388 leukemia model (see above), followed by evaluation of selected compounds in a panel of transplantable tumors (Venditti, J. M. et al., In: Garrattini S et al., eds., *Adv. Pharmacol and Chemother* 2:1-20 (1984)) including human solid tumors. The latter was made possible through the development of immunodeficient athymic nude (nu/nu) mice and the transplantation into these mice of human tumor xenografts (Rygaard, J. et al., *Acta Pathol. Microbiol. Scand.* 77:758-760 (1969); Giovanella, G. C. et al., *J. Natl Canc. Inst.* 51:615-619 (1973)). Studies assessing the metastatic potential of selected murine and human tumor-cell lines (B16, A-375, LOX-IMVI melanomas, and PC-3 prostate adenocarcinoma) and their suitability for experimental drug evaluation supported the importance of in vivo models derived from the implantation of tumor material in anatomically appropriate host tissues; such models are well suited for detailed evaluation of compounds that inhibit activity against specific tumor types. Beginning about 1990, the NCI began employing human tumor cell lines for large-scale drug screening ((Boyd, M R, In: DeVita, V T et al., *Cancer: Principles and Practice of Oncology, Updates, vol* 3, Philadelphia, Lippinicott, 1989, pp 1-12; B. Teicher, ed., *Anticancer Drug Development Guide: Preclinical Screening, Clinical Trials and Approval* chapter 2). Cell lines derived from seven cancer types (brain, colon, leukemia, lung, melanoma, ovarian, and renal) were acquired from a wide range of sources, frozen, and subjected to a battery of in vitro and in vivo characterization.

This approach shifted the screening strategy from "compound-oriented" to "disease-oriented" drug discovery (Boyd, supra). Compounds of identified by the screen, demonstrating disease-specific, differential cytotoxicity such as the anti-melanoma activity of the compounds described herein, were considered "leads" for further preclinical evaluation. A battery of human tumor xenograft models was created to deal with such needs.

The approach used to establish s.c. xenografts from human tumor cell culture lines (obtained from the NCI tumor repository at Frederick, Md.) is outlined in the schematic diagram below.

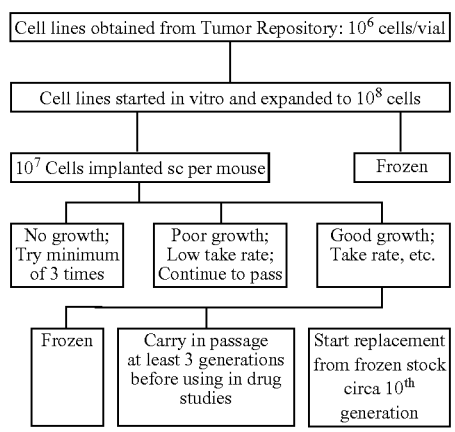

The cryopreserved cell lines are thawed, cultured in RPMI 1640 medium supplemented with 10%-heat-inactivated fetal bovine serum, and expanded until the population is sufficient to yield $\geq 10^8$ cells. Cells are harvested and then implanted s.c. into the axillary region of 10 athymic nu/nu mice ($10^7$ cells/0.5 ml/mouse). Preferred housing conditions for these mice are as follows: mice are housed in sterile, polycarbonate, filter-capped microisolator cages (e.g., from Lab. Products, Inc.), maintained in a barrier facility on 12-h light/dark cycles, and provided with sterilized food and water ad libitum. The implanted animals are observed twice weekly for tumor appearance. Growth of the solid tumors is monitored using in situ caliper measurements to determine tumor mass. Weights (mg) are calculated from measurements (mm) of two perpendicular dimensions (length and width) using the formula for a prolate ellipsoid and assuming a specific gravity of 1.0 g/cm$^3$ (Geran RI et al., *Cancer Chemother Rep.* 3, Part 3:51 (1972)). Fragments of these tumors may be subjected to histological, cytochemical, and ultrastructural analysis to monitor the characteristics of the in vivo material and to compare them with those of the in vitro lines and, where possible, with those reported for initial patient tumors (Stinson S F et al., *Anticancer Res* 12:1035-1054 (1992)). Both in vitro and in vivo tumor materials should exhibit characteristics consistent with tissue type and tumor of origin, though differences in the degree of differentiation between some of the cultured cell lines and corresponding xenograft materials are not uncommon.

The initial solid tumors established in mice are maintained by serial passage of 30-40 mg tumor fragments implanted s.c. near the axilla. Xenografts are generally not utilized for drug evaluation until the volume-doubling time has stabilized, usually around the fourth or fifth passage. The doubling time of xenografts derived from melanoma cell lines constituting both the initial (1990) and the modified (1993) human tumor cell line screens, are presented in Table 1 below. Also provided in the table is information on the take-rate of the tumors, and the experience of the NCI in the use of the tumors as early stage s.c. models. The doubling times were determined from vehicle-treated control mice used in drug evaluation experiments (data for passage numbers 4-20 are included). The doubling time is the median of the time interval for individual tumors to increase in size from 200-400 mg (usually a period of exponential growth). Both ranges and mean values are provided. Mean doubling times range from <2 d for some tumors (exemplified by the LOX-IMVI and SK-MEL-28 melanomas) to >10 d for the MALME-3M and M19-MEL melanomas.

The in vivo growth characteristics of the xenografts determine their suitability for use in the evaluation of test agent antitumor activity, particularly when the xenografts are utilized as early stage s.c. models. As used herein, an early stage s.c. model is defined as one in which tumors are staged to 63-200 mg prior to the initiation of treatment. Growth characteristics considered in rating tumors include take-rate, time to reach 200 mg, doubling time, and susceptibility to spontaneous regression. As can be noted, the faster-growing tumors tend to receive the higher ratings.

TABLE 1

Growth Characteristics of sc-Implanted Human Melanoma Xenografts

| Line | In vitro panel status 1990 | In vitro panel status 1993 | Mean volume doubling time (range) in days | Take Rate | Usefulness as early-stage sc model |
|---|---|---|---|---|---|
| LOX-IMVI | Yes | Yes | 1.5 (1.1-2-1) | Good | Good |
| SK-MEL-28 | Yes | Yes | 1.9 (1.1-2.5) | Good | Good |
| UACC-62 | Yes | Yes | 2.9 (1.9-4.2) | 70-80% | Not Acceptable |
| UACC-257 | Yes | Yes | 5.4 (3.8-7.7) | Good | Acceptable |
| SK-MEL-2 | Yes | Yes | 5.7 (4.9-6-6) | 80-90% | Not Acceptable |
| M14 | Yes | Yes | 6.7 (2.9-12.7) | Good | Acceptable |
| SK-MEL-5 | Yes | Yes | 7.3 (5.1-8-2) | Good | Acceptable |
| MALME-3M | Yes | Yes | 11.2 (7.1-16.9) | 90-90% | Not Acceptable |
| M19-MEL | Yes | No | 12.3 (8.7-16.8) | 60-90% | Not Acceptable |

Advanced-Stage Subcutaneous Xenograft Models

Such s.c.-implanted tumor xenograft models are used to evaluate the antitumor activity of test agents under conditions that permit determination of clinically relevant parameters of activity, such as partial and complete regression and duration of remission (Martin D S et al., *Cancer Treat Rep* 68:37-38 (1984); Martin D S et al., *Cancer Res.* 46:2189-2192 (1986); Stolfi, R L et al., *J. Natl Canc Inst* 80:52-55 (1988)). Tumor growth is monitored and test agent treatment is initiated when tumors reach a weight range of 100-400 mg (staging day, median weights approx. 200 mg), although depending on the xenograft, tumors may be staged at larger sizes. Tumor sizes and body weights are obtained approximately 2 times/wk. Through software programs (developed by staff of the Information Technology Branch of DTP of the NCI), data are stored, various parameters of effects are calculated, and data are presented in both graphic and tabular formats. Parameters of toxicity and antitumor activity are defined as follows:

1. Toxicity: Both drug-related deaths (DRD) and maximum percent relative mean net body weight losses are determined. A treated animal's death is presumed to be treatment-related if the animal dies within 15 d of the last treatment, and either its tumor weight is less than the lethal burden in control mice, or its net body weight loss at death is 20% greater than the mean net weight change of the controls at death or sacrifice. A DRD also may be designated by the investigator. The mean net body weight of each group of mice on each observation day is compared to the mean net body weight on staging day. Any weight loss that occurs is calculated as a percent of - the staging day weight. These calculations also are made for the control mice, since tumor growth of some xenografts has an adverse effect on body weight.

2. Optimal % T/C: Changes in tumor weight (Δ weights) for each treated (T) and control (C) group are calculated for each day tumors are measured by subtracting the median tumor weight on the day of first treatment (staging day) from the median tumor weight on the specified observation day. These values are used to calculate a percent T/C as follows:

$$\% \; T/C = (\Delta T / \Delta C) \times 100 \text{ where } \Delta T > 0 \text{ or} \quad (1)$$

$$= (\Delta T / T_I) \times 100 \text{ where } \Delta T < 0$$

and $T_1$ is the median tumor weight at the start of treatment. The optimum (minimum) value obtained after the end of the first course of treatment is used to quantitate antitumor activity.

3. Tumor growth delay: This is expressed as a percentage by which the treated group weight is delayed in attaining a specified number of doublings; (from its staging day weight) compared to controls using the formula:

$$[(T-C)/C] \times 100 \quad (2)$$

where T and C are the median times (in days) for treated and control groups, respectively, to attain the specified size (excluding tumor-free mice and DRDs). The growth delay is expressed as percentage of control to take into account the growth rate of the tumor since a growth delay based on (T−C) alone varies in significance with differences in tumor growth rates.

4. Net log cell kill: An estimate of the number of log10 units of cells killed at the end of treatment is calculated as:

$$\{[(T-C)-\text{duration of treatment}] \times 0.301/\text{median doubling time}\} \quad (3)$$

where the "doubling time" is the time required for tumors to increase in size from 200 to 400 mg, 0.301 is the $\log_{10}$ of 2, and T and C are the median times (in days) for treated and control tumors to achieve the specified number of doublings. If the duration of treatment is 0, then it can be seen from the formulae for net log cell kill and percent growth delay that log cell kill is proportional to percent growth delay. A log cell kill of 0 indicates that the cell population at the end of treatment is the same as it was at the start of treatment. A log cell kill of +6 indicates a 99.9999% reduction in the cell population.

5. Tumor regression: The importance of tumor regression in animal models as an end point of clinical relevance has been propounded by several investigators (Martin et al., 1984, 1986 supra; Stolfi et al., supra). Regressions are defined-as partial if the tumor weight decreases to 50% or less of the, tumor weight at the start of treatment without dropping below 63 mg (5×5 mm tumor). Both complete regressions (CRs) and tumor free survivors are defined by instances in which the tumor burden falls below measurable limits (<63 mg) during the experimental period. The two parameters differ by the observation of either tumor regrowth (in CR animals) or no regrowth (=tumor-free) prior to the final observation day. Although one can measure smaller tumors, the accuracy of measuring a s.c. tumor smaller than 4×4 mm or 5×5 mm (32 and 63 mg, respectively) is questionable. Also, once a relatively large tumor has regressed to 63 mg, the composition of the remaining mass may be only fibrous material/scar tissue. Measurement of tumor regrowth following cessation of treatment provides a more reliable indication of whether or not tumor cells survived treatment.

Most xenografts that grow s.c. may be used in an advanced-stage model, although for some tumors, the duration of the study may be limited by tumor necrosis. As mentioned previously, this model enables the measurement of clinically relevant parameters and provides a wealth of data on the effects of the test agent on tumor growth. Also, by staging day, the investigator is ensured that angiogenesis has occurred in the area of the tumor, and staging enables "no-takes" to be eliminated from the experiment. However, the model can be costly in terms of time and mice. For slower-growing tumors, the passage time required before sufficient mice can be implanted with tumors may be at least ~4 wks, and an additional 2-3 wks may be required before the tumors can be staged. To stage tumors, more mice (as many as 50-100% more) than are needed for actual drug testing must be implanted.

Early Treatment and Early Stage Subcutaneous Xenograft Models

These models are similar to the advanced-stage model, but, because treatment is initiated earlier in the development of the tumor, useful tumors are those with >90% take-rate (or <10% spontaneous regression rate). The "early treatment model" is defined as one in which treatment is initiated before tumors are measurable, i.e., <63 mg. The "early stage" model as one in which treatment is initiated when tumor size ranges from 63-200 mg. The 63-mg size is used because it indicates that the original implant, about 30 mg, has demonstrated some growth. Parameters of toxicity are the same as those for the advanced-stage model; parameters of antitumor activity are similar. % T/C values are calculated directly from the median tumor weights on each observation day instead of being measured as changes (Δ) in tumor weights, and growth delays are based on the days after implant required for the tumors to reach a specified size, e.g., 500 or 1000 mg. Tumor-free mice are recorded, but may be designated as "no-takes" or spontaneous regressions if the vehicle-treated control group contains >10% mice with similar growth characteristics. A "no-take" is a tumor that fails to become established and grow progressively. A spontaneous regression (graft failure) is a tumor that, after a period of growth, decreases to ≦50% of its maximum size. Tumor regressions are not normally recorded, since they are not always a good indicator of antineoplastic effects in the early stage model. A major advantage of the early treatment model is the ability to use all implanted mice, which is why a good tumor take-rate is required. In practice, the tumors most suitable for this model tend to be the faster-growing ones.

Challenge Survival Models

In another approach, the effect of human tumor growth on the lifespan of the host is determined. The LOX-IMVI melanoma has been used in this model. All mice dying or sacrificed owing to a moribund state or extensive ascites prior to the final observation day are used to calculate median day of death for treated (T) and control (C) groups. These values are then used to calculate a percent increase in life span ("ILS") as follows:

$$\% \; ILS = [(T-C)/C] \times 100 \quad (4)$$

Where possible, titration groups are included to establish a tumor doubling time for use in $\log_{10}$ cell kill calculations. A death (or sacrifice) may be designated as drug-related based on visual observations and/or the results of necropsy. Otherwise, treated animal deaths are-designated as treatment-related if the day of death precedes the mean day of death of the controls (−2SD) or if the animal dies without evidence of tumor within 15 days of the last treatment.

Response of Xenograft Models to Standard Agents

In obtaining drug sensitivity profiles for the advanced-stage s.c. xenograft models, the test agent is evaluated following i.p. administration at multiple dose levels. The activity ratings are based on the optimal effects attained with the maximally tolerated dose (<$LD_{20}$) of each drug for a given treatment schedule which is selected on the basis of the doubling time of a given tumor, with longer intervals between treatments for slower growing tumors.

The experience with melanomas described in Plowman, J. et al., supra, is summarized in Table 2 below. At least minimal antitumor effects (% T/C≦40) were produced in the melanoma group by at least 2, and as many as 10, clinical drugs. The number of responses appeared to be independent of doubling time and histological type with a range in the number of responses observed for tumors (seen in each subpanel of other tumor types as well). When the responses are considered in terms of the more clinically relevant end points of partial or complete tumor regression, these tumors models (across all tumors) were quite refractory to standard drug therapy; the tumors did not respond to any of the drugs tested in 30 of 48 (62.5%) of all tumors. The melanoma group shown was even more refractory to the standard drugs.

Strategy for Initial Compound Evaluation In Vivo

The in vitro primary screens provide a basis for selecting the most appropriate tumor lines to use for follow-up in vivo testing, with each compound tested only against xenografts derived from cell lines demonstrating the greatest sensitivity to the agent in vitro. The early strategy for in vivo testing emphasized the treatment of animals bearing advanced-stage tumors. Examples of the in vivo data obtained with one such agent (Plowman, J. et al., supra) are summarized in Table 3. A quinocarmycin derivative DX-52-1, identified as a melanoma-specific agent in vitro, demonstrated statistically significant antitumor activity against 5/7 melanoma xenografts following ip administration on intermittent schedules (Plowman J et al., *Cancer Res.* 55:862-867 (1995). The most effective in vivo activity was observed against the rapidly dividing LOX-IMVI melanoma.

TABLE 2

Response of Staged s.c. Human Melanoma Xenografts to Clinical Anticancer Drugs

| Tumor | Number of drugs active | |
|---|---|---|
| | Minimal acfivity[a] | Tumor regression[b] |
| LOX-IMVI | 7/10 | 0 |
| SK-MEL-28 | 2 | 0 |
| UACC-62 | 9 | 0 |
| SK-MEL-31 | 3/9 | 0/9 |
| UACC-257 | 7 | 0 |
| SK-MEL-2 | 7 | 0 |
| M14 | 3 | 0 |
| MALME-3M | 7 | 1 |

[a] % T/C ≦ 40
[b] % T/C ≦ 50

TABLE 3

Response of Advanced-Staged s.c. Human Melanoma Xenografts to the Quinocarmycin Derivative, DX-52-1

| Melanoma | Treatment days | Dose (ip, mg/ kg/day)[a] | Optimal % T/C (Day)[b] | Growth delay: %(T − C)/C[c] | Regressions Complete-Partial | |
|---|---|---|---|---|---|---|
| LOX-IMVI | 5, 9, 13 | 90 | −54 | 181 | 2/10 | 3/10 |
| | 5, 9, 13, 17 21, 25 | 60 | −100[b] | 389 | 4/6 | 016 |
| SK-MEL-2 | 14, 21, 28 | 90 | 10 (32) | 118 | 2/6 | 0/6 |
| SK-MEL-5 | 15, 19, 23 | 40 | 49 (33) | 27 | 0/6 | 0/6 |
| UACC-62 | 16, 23, 30 | 90 | 18 (34) | 185 | 0/7 | 0/7 |
| UACC-257 | 16, 20, 24 | 90 | 12 (27) | 35 | 0/6 | 0/6 |
| M14 | 12, 16, 20 | 90 | 19 (26) | 56 | 0/6 | 0/6 |
| MALME-3M | 27, 31, 35 | 90 | 64 (72) | 4 | 0/6 | 0/6 |

[a] Maximally tolerated dose, ≦$LD_{10}$ and <20% net body wt loss.
[b] See above for calculation of % T/C. The number in parenthesis is the day on which the optimal (minimum) T/C was attained.
[c] See above for calculation of growth delay. Based on an end point of 2 doublings (4 for LOX-IMVI).

Unless specific information is available to guide dose selection, single mice are preferably treated with single ip bolus doses of 100, 200, and 400 mg/kg and observed for 14 d. Sequential 3-dose studies may be conducted as necessary until a nonlethal dose range is established. The test agent is then evaluated preferably in three s.c. xenograft models using tumors that are among the most sensitive to the test agent in vitro and that are suitable for use as early stage models. The compounds are administered ip, as suspensions if necessary, on schedules based, with some exceptions, on the mass doubling time of the tumor. For example, for doubling times of 1.3-2.5, 2.6-5.9, and 6-10 d, preferred schedules are: daily for five treatments (qd×5), every fourth day for three treatments (q4d×3), and every seventh day for three treatments (q7d×3). For most tumors, the interval between individual treatments approximates the doubling time of the tumors, and the treatment period allows a 0.5-1.0 $\log_{10}$ unit of control tumor growth. For tumors staged at 100-200 mg, the tumor sizes of the controls at the end of treatment should range from 500-2000 mg, which allows sufficient time after treatment to evaluate the effects of the test agent before it becomes necessary to sacrifice mice owing to tumor size.

Detailed Drug Studies

Once a compound has been identified as demonstrating in vivo efficacy in initial evaluations, more detailed studies are designed and conducted in human tumor xenograft models to explore further the compound's therapeutic potential. By varying the concentration and exposure time of the tumor cells and the host to the drug, it is possible to devise and recommend treatment strategies designed to optimize antitumor activity.

The importance of "concentration x time" on the antitumor effects of test agents were well illustrated by data obtained with amino-20M-camptothecin (Plowman, J. et al., 1997, supra). Those results indicated that maintaining the plasma concentration above a threshold level for a prolonged period of time was required for optimal therapeutic effects.

Hollow-Fiber Assays: A Newer Approach to In Vivo Drug Testing

This model uses human tumor cell lines growing in hollow fibers and is intended as a prioritization tool through which lead compounds identified in an in vitro screen would pass. In brief, tumor cells are inoculated into hollow fibers (1 mm internal diameter), and the fibers are heat-sealed and cut at 2-cm intervals. These samples are maintained for 24-48 h in vitro and then implanted into nude mice. At the time of implantation, a representative set of fibers is assayed for viable cell mass by the "stable end point" MTT dye conversion technique (Alley, M C et al., *Canc Res* 51:1247-1256 (1991)) in order to determine the "time zero" cell mass for each cell line. The mice are treated with test agents on a daily treatment schedule, and the fibers are collected 6-8 d postimplantation. At collection, the quantity of viable cells contained in the fibers is measured. The antitumor effects of the test agents are determined from the changes in viable cell mass in the fibers collected from compound-treated and diluent-treated mice. Using this technique, three different tumor cell lines can be grown conveniently in each of two physiologic sites (e.g., ip and sc) within each experimental mouse. Thus, this model provides a method for administering a test agent ip to evaluate its effect against tumor cells growing in both the ip cavity and the s.c. compartment. Such simultaneous assessment of multiple tumor cell lines grown in two physiologic compartments should permit rapid identification of lead compounds with the greatest promise of clinical effectiveness.

This in vivo/in vitro hollow-fiber system may be well suited for the prioritization of compounds for more advanced stages of in vivo drug evaluation. Practically, this system can be viewed as a means to facilitate traditional chemotherapeutic testing, since it is rapid, sensitive, and is broadly applicable to a variety of human tumor cell types. Additionally, it requires only a limited quantity of test compound, a relatively small number of animals and, therefore, limited animal housing space.

Xenograft Model of Metastasis

The compounds of this invention are also tested for inhibition of late metastasis using an experimental metastasis model such as that described by Crowley, C. W. et al., *Proc. Natl. Acad. Sci. USA* 90 5021-5025 (1993)). Late metastasis involves the steps of attachment and extravasation of tumor cells, local invasion, seeding, proliferation and angiogenesis. Human melanoma cells transfected with a reporter gene, preferably the green fluorescent protein (GFP) gene, but as an alternative with a gene encoding the enzymes chloramphenicol acetyl-transferase (CAT), luciferase or LacZ, are inoculated into nude mice. This permits utilization of either of these markers (fluorescence detection of GFP or histochemical colorimetric detection of enzymatic activity) to follow the fate of these cells. Cells are injected, preferably iv, and metastases identified after about 14 days, particularly in the lungs but also in regional lymph nodes, femurs and brain. This mimics the organ tropism of naturally occurring metastases in human melanoma. For example, GFP-expressing melanoma cells ($10^6$ cells per mouse) are injected i.v. into the tail veins of nude mice. Animals are treated with a test composition at 100 μg/animal/day given q.d. IP. Single metastatic cells and foci are visualized and quantitated by fluorescence microscopy or light microscopic histochemistry or by grinding the tissue and quantitative colorimetric assay of the detectable label.

A Human Melanoma/SCID Mouse Model

Safrians, S. et al., *Int'l J. Canc.* 66:131-lf58 (1996), incorporated by reference) described studies in a human melanoma/SCID mouse model. The highly metastatic human melanoma line. C8161 (Welch et al., 1991) was transfected with antibiotic-selectable markers (with the vectors pSV2neo and pSV2hygro) using conventional methods. As clones emerged when the cells were grown in medium containing G-418 and hygromycin, the concentrations of the two agents were reduced respectively to 0.2 mg/ml and 0.1 mg/ml. Emerging clones were identified within 3-4 weeks and removed with cloning rings. Ploidy studies and karyotype analyses were performed to verify that selected clones bearing either of the two markers had no gross alterations in DNA content nor had they undergone changes in doubling time, tumorigenicity, constitutive levels of secreted collagenases, in vitro, Matrigel invasion or, most importantly, metastatic phenotype. Both neo C8161 and hyg⁻ C8161, like the parental line, demonstrate strong cytoplasmic immunoreactivity of cytokeratins 8 and 18, which facilitates their detection within the organs.

Between $5 \times 10^4$ and $5 \times 10^6$ neo⁻ and/or hyg⁻ C8161 cells suspended in 0.2 ml Hanks' balanced salt solution (HBSS) are injected either s.c. in a right dorsolateral flank region (assay for spontaneous metastasis) or i.v. in the tail vein (hematogenouso metastasis) or via both routes at successive intervals. Animals are killed at various intervals (preferably ranging from 2 to 8 weeks), the organs are removed and metastatic colonies are quantified to determine the distribution of tumor cells from hematogenous dissemination. The size of the primary tumor as well as the number and distribution of metastases are determined.

Representative mice are subjected to histopathological and immunocytochemical studies to further document the presence of metastases throughout the major organs. Number and size (greatest diameter) of the colonies can be tabulated by digital image analysis, e.g., as described by Fu, Y. S. et al., *Anat. Quant. Cytol. Histol.* 11:187-195 (1989)).

For determination of colonies, explants of lung, liver, spleen, para-aortic lymph nodes, kidney, adrenal glands and s.c. tissues are washed, minced into pieces of 1-2 mm³ and the pieces pulverized in a Tekman tissue pounder for 5 min. The pulverized contents are filtered through a sieve, incubated in a dissociation medium (MEM supplemented with 10% FCS, 200 U/ml of collagenase type 1 and 100 μg/ml of DNase type 1) for 8 hr at 37° C. with gentle agitation. Thereafter, the resulting cell suspension is washed and resuspended in regular medium (e.g., MEM with 10% FCS supplemented with the selecting antibiotic (G-418 or hygromycin). The explants are fed as described by Safrians et al., supra, and the number of clonal outgrowths of tumor cells is determined after fixation with ethanol and staining with a monoclonal antibody to cytokeratins 8 and 18. The number of colonies is counted over an 80-cm² area. If desired, a parallel set of experiments can be conducted wherein clonal outgrowths are not fixed and stained but rather are retrieved fresh with cloning rings and pooled after only a few divisions for other measurements such as secretion of collagenases (by substrate gel electrophoresis) and Matrigel invasion.

Modified Matrigel invasion assays are performed as described by others (Hendrix, M. J. C. et al., *Cancer Lett.*, 38:137-147 (1987); Albini, A. et al., *Cancer Res.*, 47 3239-3245 (1987); Melchiori, A., *Cancer Res.* 52:2353-2356 (1992)). Substrate gel electrophoresis of conditioned media from the aforementioned clones are analyzed as described by others (Herron, G. S. et al., *J. Biol. Chem.* 261:2814-2818 (1986); Ballin, M. et al., *Biochem. Biophys. Res. Comm.*, 154:832-838 (1988)).

All experiments are performed with groups that preferably have 10 mice. Results are analyzed with standard statistical tests. C8161 cells demonstrate significant numbers of both spontaneous and hematogenous metastasis. Significant numbers of hematogenous metastases may be produced almost exclusively in the lungs with an injection of $5 \times 10^5$ cell (and larger numbers result in extrapulmonary metastases).

Safrians et al., supra, found that i.v. injections of 5×10[5] tumor cells 1 week after an s.c. flank injection of an equal number of tumor cells followed by an additional 5-week interval yielded a ratio of 2:1 hematogenous:spontaneous pulmonary metastases and an overall pulmonary tumor burden of 1.25 g (over a normal pulmonary weight: 0.2 g). With this regimen, numerous extrapulmonary metastatic clones could be retrieved from spleen, liver, kidneys, adrenal gland, para-aortic lymph nodes and s.c. sites. The vast majority of these clones represent spontaneous metastases from the locally growing tumor. Similar results were obtained with C8161 carrying either of the antibiotic resistance markers discussed above.

3. Transgenic Mouse Model

A useful murine melanoma model in which dominantly acting oncoproteins are somatically regulated in vivo was developed by Chin, L. et al., *Nature* 400:468-472 (1999 July). Cohorts of single and double transgenic mice (designated Tyr/Tet-Ras) homozygous null for the INK4a gene (INK4a$^{-/-}$) were generated.

Production of the Transgenic Mice

The reverse tetracycline transactivator (rtTA) is a 1,050 bp EcoRI/BamHI fragment isolated from pUHDI72-Ineo (Gossen, M. et al., *Science* 268:1766-1769 (1995)). The Tet promoter contains an XhoI/EcoRI fragment of the cytomegalovirus minimal promoter linked to the tet operator sequence. The tyrosinase enhancer/promoter and the H-Ras$^{Val12}$ transgene were as described in Fasano, O. et al., *J. Mol. Appl. Genet.* 2:173-180 (1983); Chin, L. et al., *Genes Dev.* 11:2822-2834 (1997); and Ganss, R. et al., *EMBO J.* 13:3083-3093 (1994). Fasano, O. et al., *J. Mol. Appl. Genet.* 2:173-180 (1983). Chin, L. et al. (*Nature* 400:468-472 (1999)) generated multiple founder lines for both transgenes and used one activator line (Tyr/rtTA, line 37) and two independent reporter lines (Tet-RAS, lines 65 and 72) for further development.

Primary Tumors, Derivative Cell Lines and SCID Explant Tumors

Transgenic mice are fed doxycycline drinking water (2 mg/ml in sucrose water) and observed for spontaneous tumor development. Primary tumors are adapted to culture by mechanical mincing with sterilized razor blades and brief trypsinization, and maintained in RPMI medium containing 10% serum and supplemented with doxycycline (2 µg/ml medium) (Kistner, A. et al., *Proc. Natl. Acad. Sci USA* 93:10933-10938 (1996)).

For the SCID explant tumors, 2-5×10[6] established melanoma cell are injected s.c. into the flanks of adult SCID mice maintained on doxycycline or regular drinking water. These cell lines are passaged sufficiently to insure elimination of immunocytes from the original host.

Development of Melanomas after Doxycycline Treatment

As indicated above, double transgenic mice are generated by intercrossing INK4a$^{+/-}$ mice with either (a) a transgenic mouse line harboring the rtTA under the control of the tyrosinase gene promoter/enhancer elements (designated Tyr-rtTA), or (b) a transgenic mouse line containing the H-Rasv$^{V12G}$ open reading frame driven by a minimal promoter containing multimerized tet-operons, designated Tet-Ras (Gossen et al., supra; Fasano et al., supra).

In the doxycycline-treated group, about 25% of double transgenic Tyr/Tet-Ras INK4a$^{-/-}$ mice 5 develop melanomas (average latency: 60 days). In contrast, untreated Tyr/Tet-Ras INK4a$^{-/-}$ mice or treated single transgenic Tet-Ras INK4$^{-/-}$ mice do not develop melanomas.

The Tyr/Tet-Ras INK4a$^{-/-}$ animals' melanomas shared all of the macroscopic features of the melanomas of constitutive Tyr-Ras INK4a$^{-/-}$ mice, manifesting as amelanotic, invasive and highly vascular tumors, reminiscent of nodular-type melanoma in humans. Characteristics include spindle morphology with anaplastic and pleiomorphic cytology, and strong immunoreactivity to the early melanocyte-specific marker tyrosinase-related-protein-I (TRP-1) (Thomson, T. M. et al., *J. Invest. Dermatol* 90:459-466 (1988)). Tumors and cultured cell lines derived therefrom express strong H-Ras$^{V12G}$ expression and activity.

These double transgenic animals that can be induced to develop melanoma are treated in accordance with the present invention to evaluate the anti-melanoma activity of the agents described herein.

For a compound to be useful in accordance with this invention, it should demonstrate activity in at least one of the in vitro or in vivo assay systems described herein.

Having now generally described the invention, the same will be more readily understood through reference to the following examples which are provided by way of illustration, and are not intended to be limiting of the present invention, unless specified.

EXAMPLE I

Materials and Methods for Studies of Melanoma Cells

Cell Lines, Reagents and Treatments

Human melanoma cell lines used in this study were obtained from NCI-ADS and cultured as described (Monks, A. et al. *J. Natl Canc Inst* 83:757-766 (1991)). Normal neonatal human epidermal melanocytes (NHEM 2489) were purchased from Clonetics and cultured in Melanocyte Growth Medium-3 (Clonetics) as suggested by the manufacturer. Purified recombinant protective antigen (PA), lethal factor (LF) and edema factor (EF) were provided by Stephen H. Leppla (National Institute of Dental Research, NIH, USA) and were used to treat cells at 0.1 µg/ml each in the appropriate culture medium. Control groups were treated with PA alone, which functions as a translocator for LF and EF (Leppla, S. H., supra; Duesbery, N. S. et al., 1999, supra). When treating with LF or EF, their respective toxin complexes that included PA were used ("LF+PA" and "EF+PA"). For normal melanocytes, additional LF+PA or PA alone (0.1 µg/ml each) was added directly to the medium 72 hours after the initial treatment, and the cells were incubated for an additional 24 hours.

PD98059 (New England Biolabs, Inc.) was dissolved in dimethyl sulfoxide (DMSO), and 20 mM aliquots were stored at −20° C. To maintain sustained inhibition of MEKs, PD98059 was directly added to the cultures every 24 hours to achieve a final concentration of 20 µM for the duration of the study, unless otherwise indicated. IBMX (Calbiochem Co.) dissolved in DMSO was added to the appropriate culture medium at a final concentration of 200 µM. An equivalent volume of DMSO solvent was added to controls. U0126 (Promega Corp) was dissolved in DMSO to 10 mM, and a single dose, final concentration of 10 µM, was used.

Quantitation of Apoptosis

Apoptosis was quantified as described previously (Koo, H.-M. et al. *J Natl Canc Inst* 91:236-244 (1999); Koo, H.-M. et al. *Canc Res* 59:6057-6062 (1999)). Briefly, total cells including floating cells were collected, washed in phosphate-buffered saline (PBS), and fixed in 10% formalin. The fixed cells were washed in PBS, and then mounted onto a polylysine-coated glass slide by Cytospin centrifugation. The mounted cells were stained for DNA with 4'6-diamidine-2'-phenyline dihydrochloride (DAPI) and examined by fluorescent microscopy. A total of 300-500 nuclei from several random fields were examined, and apoptosis was expressed as a percentage of the nuclei displaying apoptosis-associated morphological changes.

Flow Cytometry

Cell cycle profiles and DNA content were analyzed by flow cytometry, as previously described (Koo, H.-M. et al. *Canc Res* 59:6057-6062 (1999)). Total cells including floating cells were harvested, washed in cold PBS and fixed in cold 70% ethanol overnight. The fixed cells were rehydrated in PBS containing 1% fetal bovine serum, washed in PBS, incubated with DNase-free RNase at room temperature for 30 min, and then stained with 50 µg/ml propidium iodide overnight at 4° C. in the dark. The stained samples were analyzed in a FACSCalibur (Becton Dickinson Biosciences) for DNA content and cell cycle profiles.

Western Immunoblotting

Western blot analysis was performed as described previously (Koo et al., 1999, supra). The primary antibodies used were anti-active MAPK from Promega, and anti-ERK1 (K-23) and anti-ERK2 (C-14) from Santa Cruz Biotechnology.

Determination of Melanin Content

Intracellular melanin was solubilized by lysing cells in 0.2N NaOH and incubating at 60° C. for 1 hour. The relative absorbance at 405 nm for melanin to that at 280 nm for protein was calculated ($A_{405}/A_{280}$). The control relative absorbance, "$A_{405}/A_{280}$ (PA alone)" was set to 1.0. The melanin content in each treatment group was expressed as the ratio $$\frac{A_{405}/A_{280}(\text{experimental})}{A_{405}/A_{280}(PA \text{ alone})}$$

To visualize melanization, $4 \times 10^6$ cells from each group were concentrated in a well of 96-well microplate and photographed (e.g., FIG. 5).

In Vivo Testing of LF on M14-MEL or SK-MEL-28 Xenografts in Athymic Nude Mice

Female athymic nude (nu/nu) mice (~8 weeks old) were injected s.c. with M14-MEL or SK–MEL-28 cells ($10^7$ cells/mouse). When tumors grew to an average mass of 95 mg in the earlier experiment or about 450 mm³ for M14-MEL and about 310 mm³ for SK-MEL-28 in the latter experiments, the control group (n=6) was treated with PA (6 µg/mouse) alone by daily intratumoral injection for 13 days. During the same period, the test group (n=7) was treated first with 6 µg PA+2 µg LF/mouse for 4 days and then continued with 6 µg PA+4 µg LF/mouse for another 9 days. M14-MEL xenograft tumors (n=6) were treated with 7 doses, and SK-MEL-28 tumors (n=7) with 5 doses and then each animal was given an additional dose three days later. Tumor weight was calculated by the formula: $(L \times W^2)/2$. The experiment was terminated when a majority of mice in the control group showed a significant weight loss (>10% of body weight) or when control tumors reached about 2000 mm³.

Histology and In Situ TUNEL Staining

Dissected tumors were fixed in 10% neutral-buffered formalin overnight, embedded in paraffin blocks, cut into thin (5 µm-thick) sections and then mounted on glass slides. After deparaffinization and rehydration, tumor sections were stained with hematoxylin and eosin (H&E) or for TUNEL. TUNEL staining was performed using "In Situ Cell Death Detection, POD kit (Roche Molecular Biochemicals) as recommended by the manufacturer. Tumor sections were counter-stained with hematoxylin. TUNEL-positive areas stain dark brown and nuclei (or DNA) stain light-blue

EXAMPLE II

MEK-Directed Protease LF and PD98059 Induce Apoptosis in Different Human Melanoma Cell Lines Following 72-hour incubation, all melanoma cell lines tested underwent a variable degree of apoptosis in response to LF (FIG. 1). The same cohort of melanoma cell lines was also treated with PD98059. For this experiment, the cells were repeatedly exposed to the inhibitor every 24 hours for 72 hours, because of instability of the compound in culture medium Dudley, D. T. et al., *Proc Nat'l Acad Sci USA* 92:7686-7689 (1995); Alessi, D. R. et al., *J Biol Chem* 270: 27489-27494 (1995)) Again, all of the cell lines responded to the MEK inhibitor by apoptosis (FIG. 2).

With the exception of the LOX-IMVI cells, which express different genes from melanoma cells (Stinson, S. F. et al., *Anticancer* 12:1035-1054 (1992); Ross, D. T. et al., *Nature Genetics* 24:227-235 (2000)) the relative sensitivities of the melanoma lines to apoptosis induced by LF and PD98059 were similar (cf. FIG. 1 and FIG. 2).

Apoptosis could mostly account for the enhanced sensitivity of human melanoma cell lines in the NCI-ADS to LF or PD98059.

Figure 15:
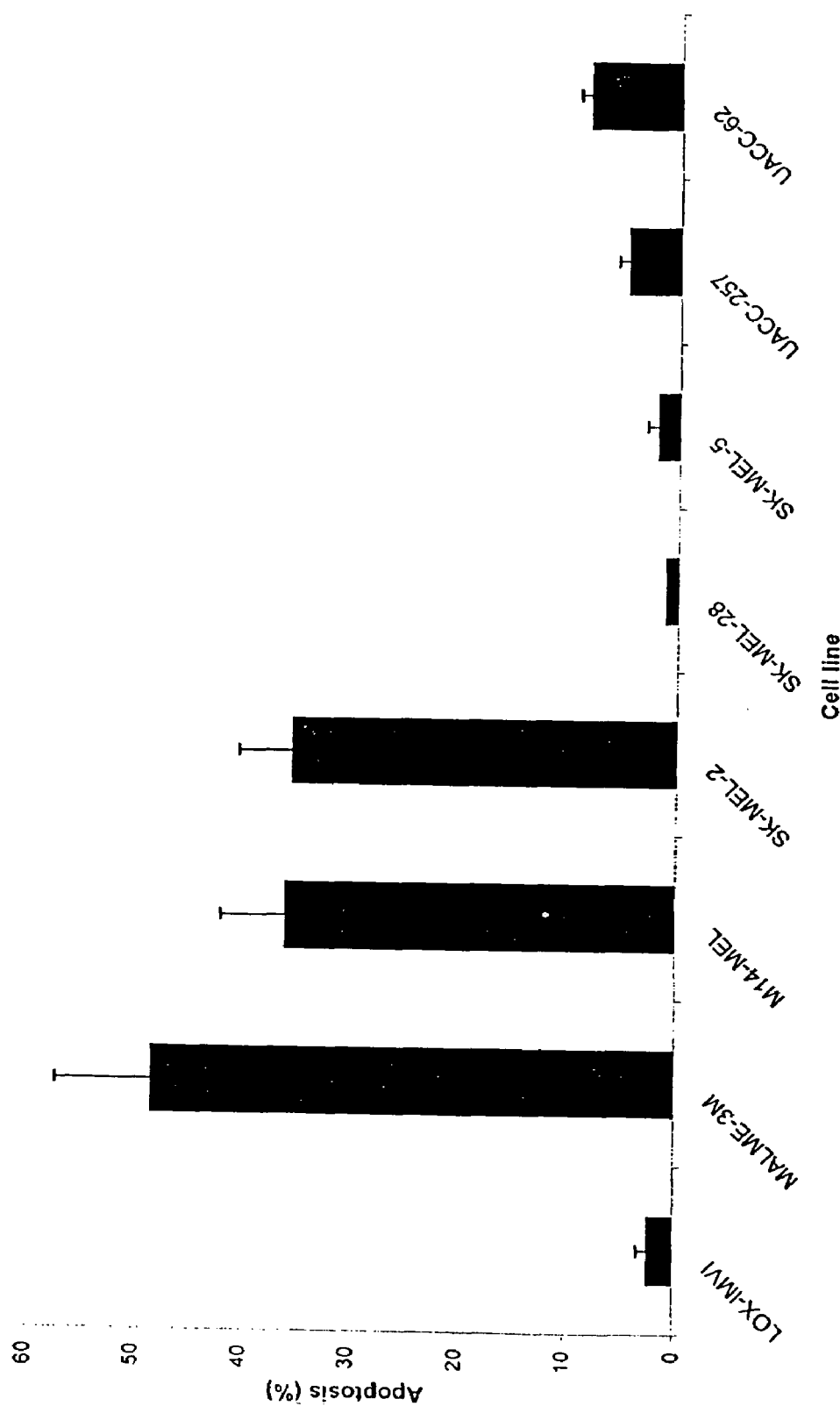
FIG. 15 is a graph showing apoptosis induced by the MEK inhibitor U0126 (10 μM, single inoculation). Apoptosis was quantified by staining DNA with DAPI followed by examining nuclear morphology of the stained cells. Standard deviations (of quadruplicate samples) are shown.
Figure 16A:
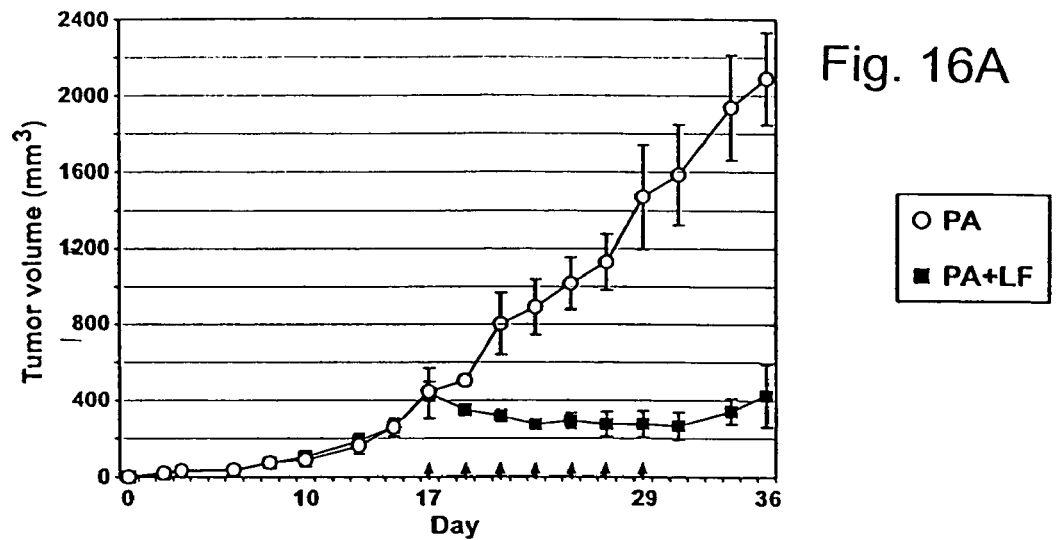
FIGS. 16A and 16B show in vivo effects of LF treatment on M14-MEL (FIG. 16A) or SK- MEL-28 (FIG. 16B) melanoma xenograft tumor growth. When xenograft growth was established, the tumors were treated with 6 μg PA+2 μg LF/mouse (PA+LF, ■) or 6 μg PA/mouse as controls (PA, 0) every other day. Tumor volume ($mm^3$) is shown along with standard deviations. (Panel A) M14-MEL xenograft tumors (~450 $mm^3$) were treated with 7 doses (d.17-29, indicated by ↑ above x-axis). (Panel B) SK-MEL-28 tumors (~310 mm3) were treated with 5 doses (d.27-35, indicated by ↑ above x axis) and then with an additional dose three days later (d.38, indicated by ⇓). The LF-treated tumors remained in complete regression for over 4 weeks (d.65). Both graphs were plotted in the same scale.
Figure 16B:
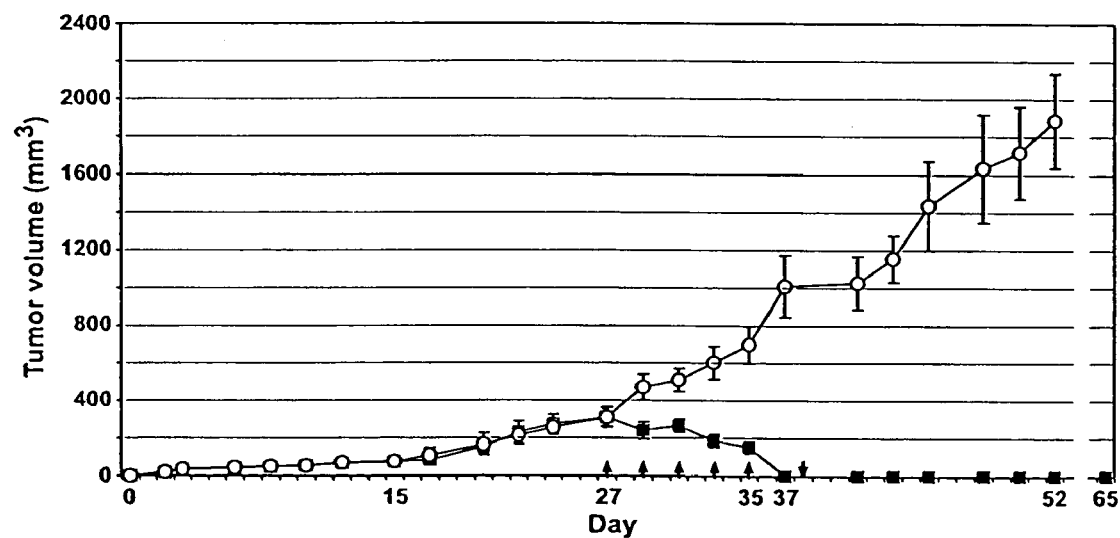
Figure 18:
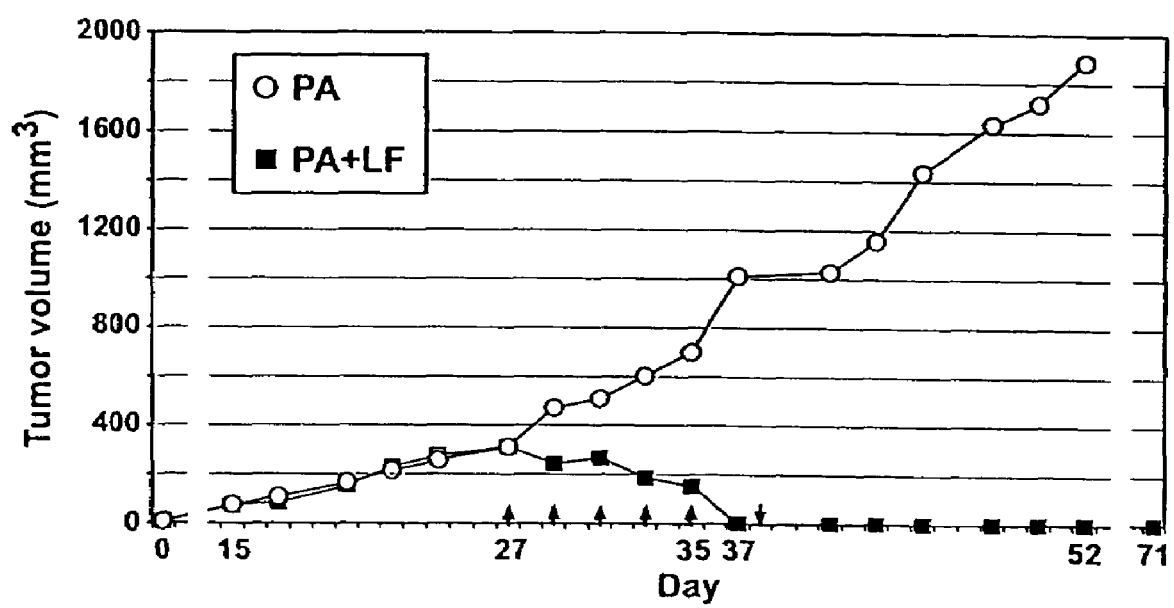
FIG. 18 shows the effect of LF treatment of SK-MEL-28 human melanoma xenografts in nude mice by direct intratumoral injection. When tumor growth was established (volume of ~310 $mm^3$ on day 27 after implantation), tumors were treated with 6 μg PA+2 μg LF/mouse (PA+LF, ■) or 6 μg PA/mouse as controls (PA, ○). Five doses were given at 2-day intervals (days 27-35, ↑) and then an additional dose three days later (day 38, ⇓). Standard deviations (SD) of PA-treated tumors, ranged from 48 $mm^3$ (day 27) to 250 $mM^3$ (day52); SD's of PA+LF-treated tumors ranged from 56 $mm^3$ (day 27) to 32 $mm^3$ (day 35).

Another MEK inhibitor, U0126, also induced apoptosis in these melanoma lines with a similar pattern (FIG. 15).

These results demonstrate that human melanoma cells are especially sensitive to apoptosis triggered by inhibition of MAPK signaling. This is unlike most other cell types so far tested, which, in response to the MAPK signal blockade, display cytostatic growth inhibition without cell death both in vitro and in vivo (Cohen, P. *Curr Opin Chem Biol* 3:459-465 (1999); Roussel, M. F., *Adv Canc Res,* 74:1-24 1998); Sebolt-Lepold, J. S. et al., supra.

EXAMPLE III

Inhibition of MAPK Activation Affects Melanoma Cell Cycle Progression

In most cell types, activation of the MAPK pathway is required for progression through the restriction point in G1 phase of the cell cycle (reviewed in Roussel et al., supra). To investigate the effect of inhibition of MAPK activation on melanoma cell cycle progression, cell cycle changes and apoptosis were monitored in a representative melanoma cell line (MALME-3M) during a 72-hour exposure to LF or PD98059.

Within 24 hours of the treatment with LF or PD98059, cell cycle progression was noticeably blocked in the G1 phase (FIGS. 3B and 3E). Both agents induced apoptosis by 48 hours, and a significant fraction of the cells (>25%) were undergoing apoptosis by 72 hours (FIGS. 3C, 3D, 3F and 3G).

Figure 4:
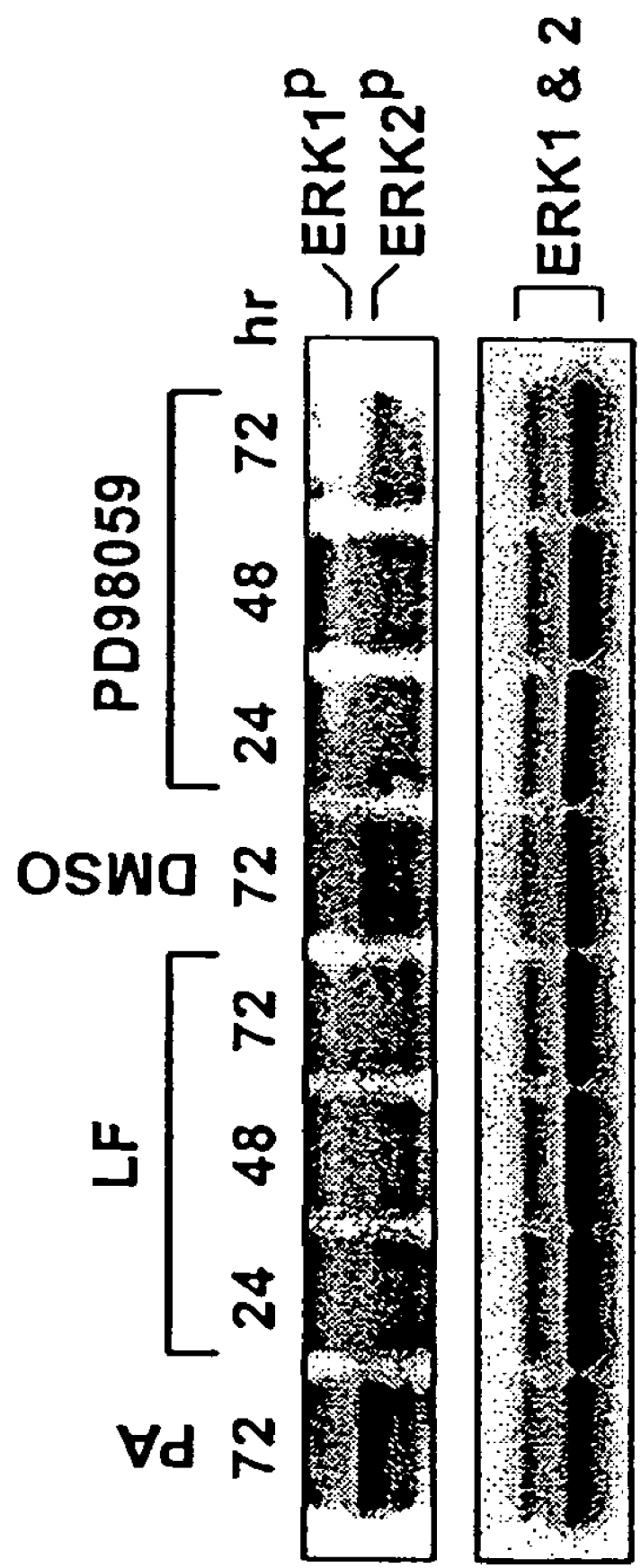
FIG. 4 is an immunoblot of active phospho-MAPK in MALME-3M cells treated with LF or PD98059 for the indicated durations (hours). Controls were treated with protective antigen ("PA") of the anthrax toxin complex alone or with DMSO for 72 hours. As loading control, the blot was stripped and re-probed with anti-MAPK antibodies (1:1 mixture of anti-ERK1 and ERK2 antibodies) shown in the lower panel). Results indicated equivalent loading of the gels with MAPK.

Continuous accumulation of the cells in G1 phase was noted as evidenced by a decrease in the percentage of cells in the S and G2/M phases (FIG. 3A-3G). In both LF and PD98059-treated cells, activation of ERK1 and 2 was inhibited (FIG. 4).

After a 72-hour incubation with LF or PD98059, a similar response of apoptosis and G1 arrest, coinciding with downregulation of ERK activation was observed in all the other human melanoma cell lines examined (see Table 4). Nevertheless, these responses were reversible since, even after 72-hours with LF or PD98059, removal of the inhibitors allowed restoration of ERK activation and resumption of normal cell cycle progression.

It was concluded that sustained inhibition of the MAPK signaling pathway is required to effectively trigger apoptosis in human melanoma cells.

EXAMPLE IV

Induced Melanoma Cell Differentiation and Apoptosis

Both LF and PD98059 were found to induce melanin production in the melanotic melanoma cell lines tested. Melanogenesis is induced during melanocyte (and melanoma cell) differentiation (Busca, R. et al. *Mol Biol Cell* 9:1367-1378 (1998)). Inhibition of the MAPK pathway was known to induce differentiation of B16 mouse melanoma cells (Englaro, W. et al. *J Biol Chem* 273:9966-9970 (1998)). These findings suggested that apoptosis may be associated with terminal differentiation induced by inhibition of the MAPK pathway. To address this possibility, cyclic AMP (cAMP)-elevating agents that induce melanoma cell differentiation (Busca et al., supra, and reference cited therein) were examined for their effects on melanogenesis and apoptosis induced by LF or PD98059 in the melanotic UACC-257 and MALME-3M cell lines.

The cAMP-elevating agents used were the edema factor (EF) of *Bacillus anthracis*, an adenylyl cyclase (Leppla, supra; Duesbery et al., supra), and isobutylmethylxanthine (IBMX), a phosphodiesterase inhibitor (Beavo, J. et al., *Trends Pharmacol Sci* 11:150-155 (1990)).

Figure 6:
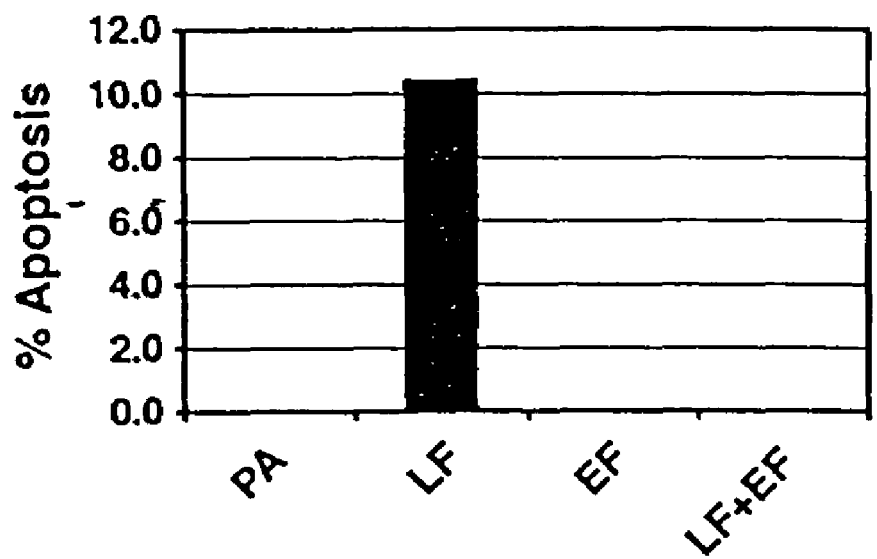
FIG. 6 shows the antagonistic effect of EF on apoptosis triggered by LF in UACC-257 cells.

Neither EF nor IBMX treatment induced significant melanogenesis in the human melanoma cell lines examined. However, combination of EF or IBMX with LF or PD98059 caused a synergistic effect on the melanin production (FIGS. 5 and 6). Morphological changes (dendrite formation) induced by LF or PD98059 was also enhanced by EF or IBMX in both melanoma lines.

The cooperation between LF and EF on melanization may explain the formation of a blackened eschar in the skin lesion of anthrax infection site (Leppla, supra; Duesbery et al., supra). See the photographs (circles) in FIG. 5A.

Figure 7:
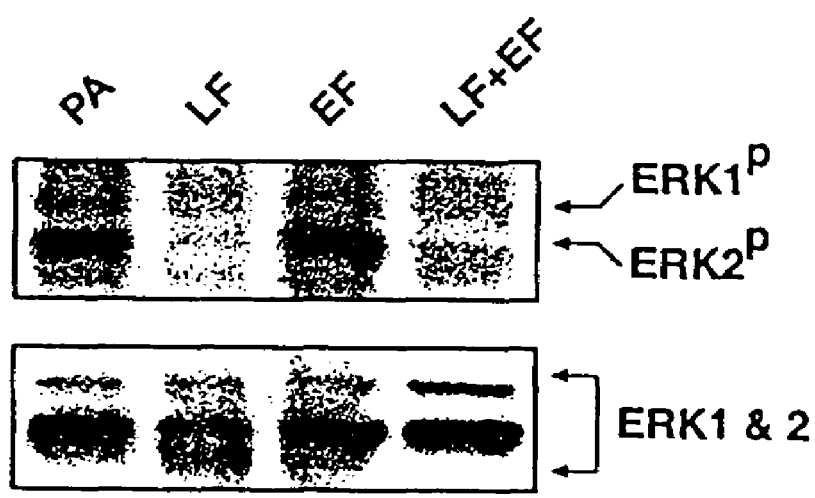
FIG. 7 shows active phospho-MAPK immunoblots of the duplicate UACC-257 cells treated as described for FIGS. 5A, 5B and 6. Loading controls were performed as described for FIG. 4
Figure 8:
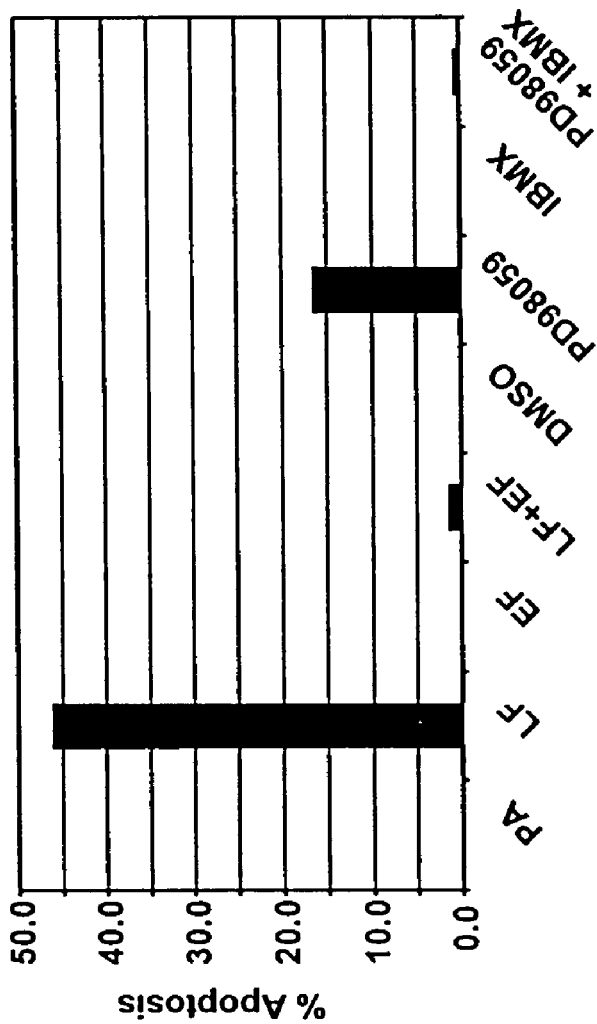
FIG. 8 shows the antagonistic effect of EF on apoptosis triggered by LF and the antagonistic effect of IBMx on apoptosis triggered by PD98059 in MALME-3M cells

In contrast, apoptosis induced by LF or PD98059 was severely antagonized by simultaneous treatment with EF or IBMX (FIGS. 6 and 8). This antagonism occurred even though activation of ERK1 and 2 was significantly inhibited (FIGS. 7 and 9).

Figure 9:
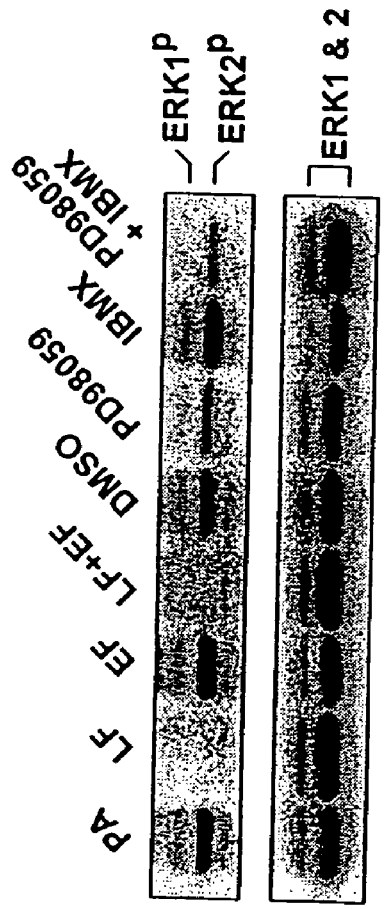
FIG. 9 shows active phospho-MAPK immunoblots of the duplicate MALME-3M cells treated as described for FIGS. 5A, 5B and 8. Loading controls were performed as described for FIG. 4.
Figure 10:
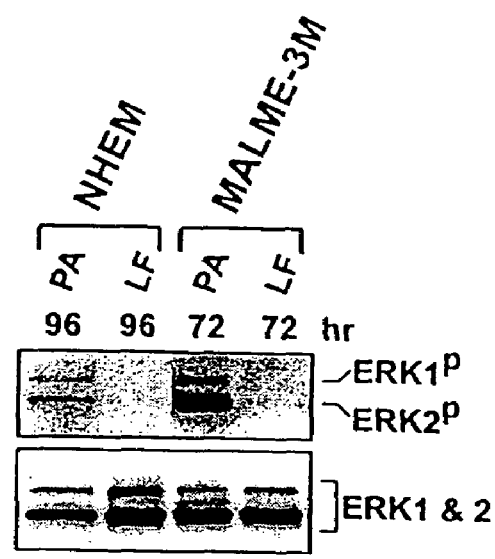

The partial inhibition (or restoration) of activation of ERK1/2 by PD98059 was sufficient to trigger apoptosis in MALME-3M cells, whereas the greater degree of inhibition produced by the combination of PD98059+IBMX was not apoptotic (FIG. 9).

A similar antagonistic effect of EF on LF-induced apoptosis was observed in all the other human melanoma cell lines tested.

These results demonstrated that apoptosis in melanoma cells was not merely a "byproduct" of the differentiation induced by inhibiting MAPK signaling. These results suggested that (1) an event or events downstream from MAPKs is or are responsible for the apoptotic response of γmelanoma cells and (2) this event(s) is dominantly modulated by a cAMP-dependent pathway.

TABLE 4

LF and Low Molecular Weight MEK Inhibitors PD98059 and U0126 Induced Apoptosis in Human Melanoma Cell Lines.

| Melanoma | Experiment I Apoptosis SD (%) | | | | | Experiment II Apoptosis (%) | |
|---|---|---|---|---|---|---|---|
| cell lines | LF | | PD98059 | | U0126 | LF | LF + EF |
| LOX-IMVI* | 49.2 | 4.5 | 3.6 | 1.8 | 2.3 | 1.8 | 47.2 | 20.8 |
| MALME-3M | 55.2 | 2.6 | 47.9 | 3.3 | 48.3 | 10.3 | 31.5 | 1.9 |
| M14-MEL | 51.9 | 0.9 | 53.0 | 2.7 | 36.0 | 8.7 | 37.1 | 42.4 |
| SK-MEL-2 | 14.9 | 3.0 | 23.4 | 2.3 | 35.4 | 4.4 | 19.1 | 8.5 |
| SK-MEL-28 | 8.2 | 1.4 | 2.5 | 0.6 | 1.1 | 0.2 | 8.4 | 0 |
| SK-MEL-5 | 6.7 | 0.6 | 9.1 | 1.2 | 1.9 | 0.5 | 3.7 | 1.5 |
| UACC-257 | 8.6 | 1.1 | 19.7 | 4.0 | 4.7 | 1.2 | 32.1 | 1.0 |
| UACC-62 | 28.1 | 1.2 | 30.5 | 1.8 | 8.3 | 0.9 | 20.4 | 17.3 |

*LOX-IMVI cells display the surface antigen and gene expression profiles different from other melanoma cells used in NCI-ADS (Ross et al., Nature Genetics 24: 227-235, and Stinson et al., Anticancer 12: 1035-1054).
Experiment I: Percentage apoptosis shown is an average of four replicates minus background apoptosis (PA alone or DMSO). Standard deviation (SD) of the replicate samples is indicated.
Experiment II: Percentage apoptosis was quantified from a single sample treated with each toxin. EF by itself did not induce apoptosis in the melanoma cell lines.

The results with a different small molecule inhibitor of MEK inhibitor, PD184352 (Sebolt-Leopold et al., supra) are shown in Table 5, below.

TABLE 5

Dose-Dependent Apoptotic Response of Human M14-MEL Melanoma Cells to PD184352

| Treatment for 72 hours | | % Apoptosis |
|---|---|---|
| M14-MEL Melanoma Cells | | |
| DMSO | | 0.6 |
| PD98059 | 20 μM | 38.9 |
| PD184352 | 1 μM | 24.5 |
| PD184352 | 5 μM | 37.3 |
| PD184352 | 10 μM | 48.8 |
| PD184352 | 20 μM | 71.0 |
| Normal Melanocytes | | |
| DMSO | | 0 |
| PD98059 | 20 μM | 0 |
| PD184352 | 2 μM | 0.3 |

The above results show that PD184352 is selectively cytotoxic to human melanoma cells in comparison to normal human melanocytes and that this cytotoxic action occurs via apoptosis. Indeed this compound acts in a dose-dependent manner and appears to be more potent, possibly by several fold, than PD98059

Western blot analysis with a phospho-specific anti-ERK antibody confirmed that activation of MAPK (ERK1/2) was completely blocked by PD184352 in M14-MEL melanoma cells.

EXAMPLE V

Inhibition of MAPK Signaling in Normal Human Melanocytes

Figures 12A, 12B, 12C, 12D:
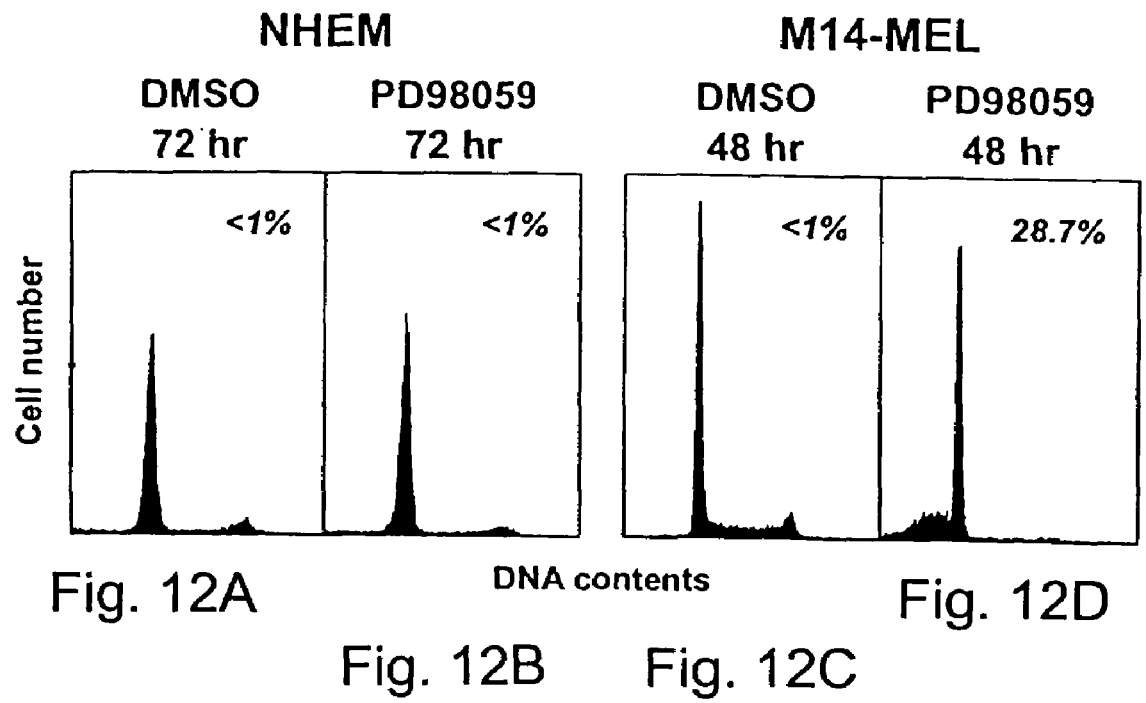
FIGS. 12A-12D are cytograms and FIG. 13 is an immunoblot demonstrating the effects of MAPK signal inhibition on normal human melanocytes. NHEM cells or M14-MEL melanoma cells were cultured in Melanocyte Growth Medium-3 (Clonetics). NHEM cells were treated with PD98059 for 72 hours. M14-MEL melanoma cells were treated either with PD98059 for 48 hours. Controls were treated with DMSO.
Figure 13:
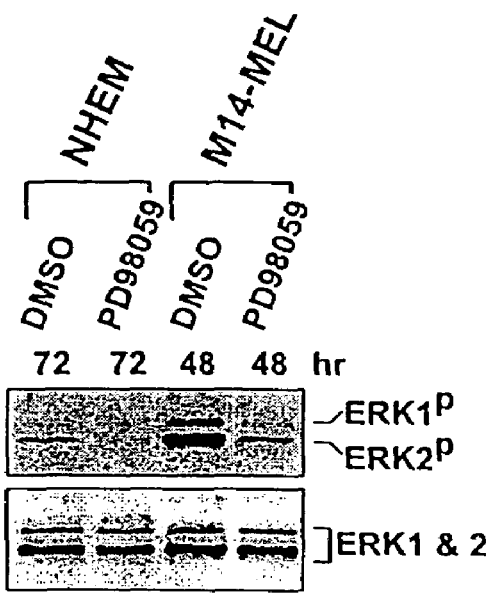
Figure 14:
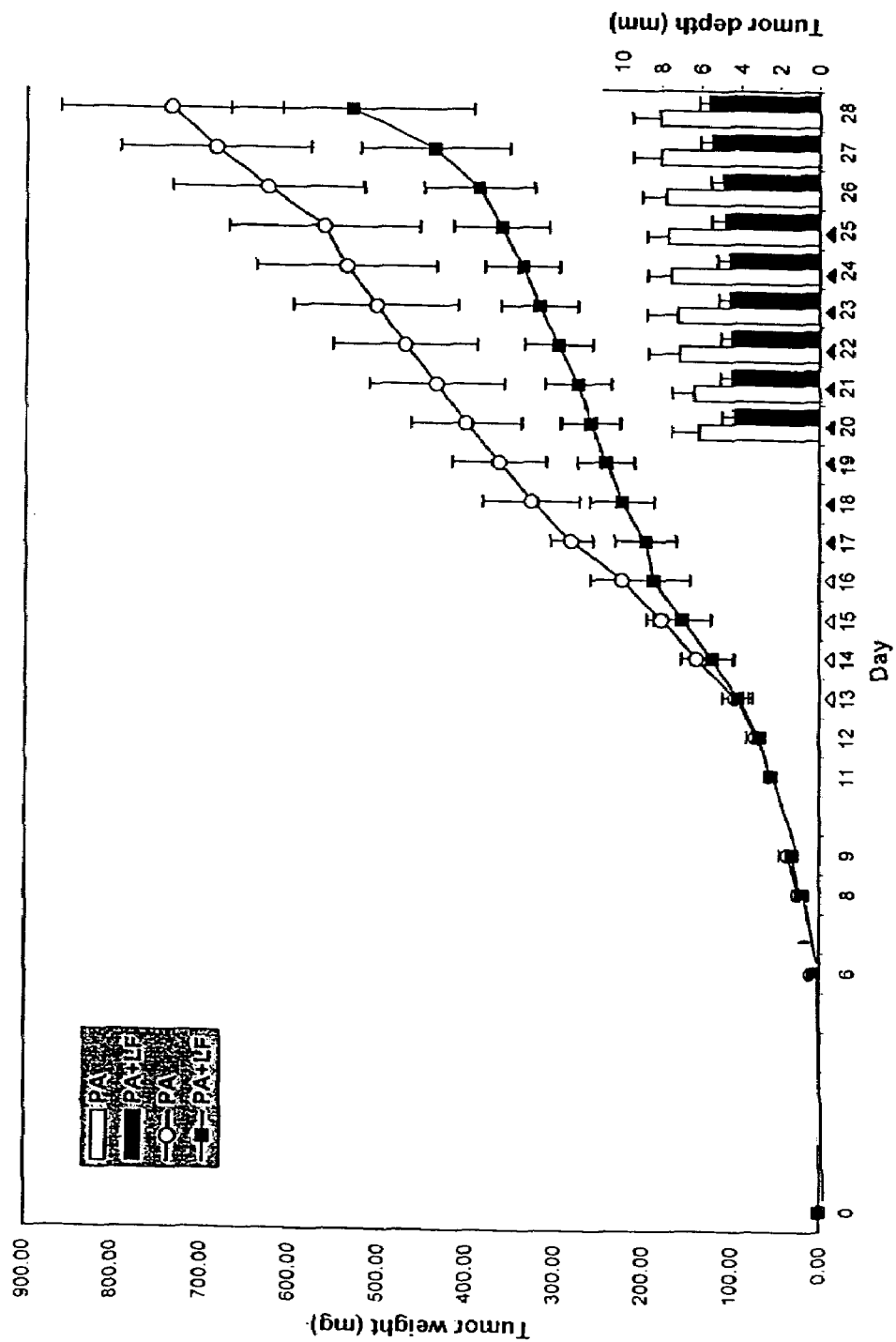
FIG. 14 is the graph showing in vivo effect of the MEK-directed protease LF on human melanoma M14-MEL xenografts in athymic nude mice. Results are shown as estimated tumor weights. When tumors reached an average of 95 mg in mass, one group (n=6) was treated with PA (6 μg/mouse) alone daily for 13 days (d.13-25) as control. Mice of the other group (n=7) were treated daily, first with 6 μg PA+2 μg LF/mouse for 4 days (Δ: days 13-16) and then with 6 μg PA+4 μg LF/mouse for the remaining 9 days (▲: days 17-25). See Example I for methods. Tumor weight (line graph), and tumor depth in mm (column graph inset) are shown along with standard deviations.

Incubation of normal melanocytes for 72 hours with PD98059 (and U0126) or 96 hours with LF induced $G_1$ arrest, and while MAPK activation was inhibited, no apoptosis was observed (FIGS. 12B and 13).

Figures 11A, 11B, 11C, 11D:
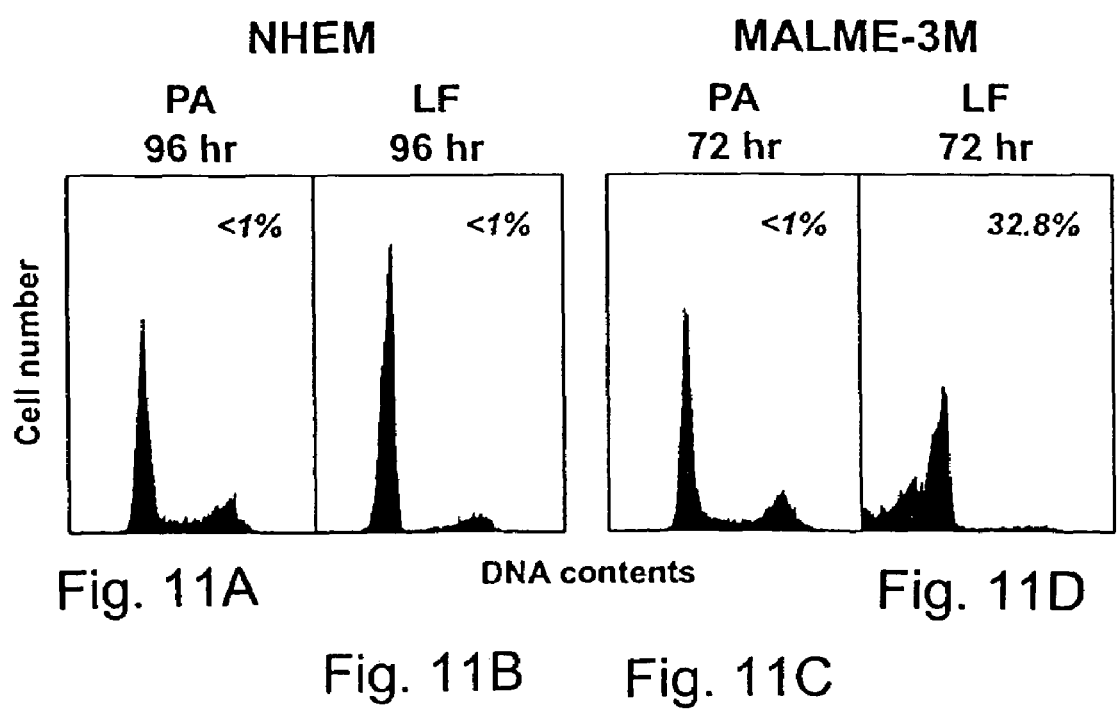

A 96-hour incubation with LF completely inhibited ERK activation (FIG. 9), but no apoptosis was detected (FIG. 11B).

In contrast, a shorter (72 hours) incubation with LF triggered apoptosis in a representative melanoma cell line (FIG. 11D). Similarly, apoptosis was not detected in normal melanocytes treated with PD98059 for 96 hours (FIG. 11B). These results indicate that the MAPK cascade generates or mediates a survival signal that is specific to malignant melanoma cells and that is not essential for survival of normal melanocytes in culture.

This is consistent with the findings of Chin, L. et al (Nature 400:468-472 (1999)) that in a mouse melanoma model null for INK4a and containing a doxycycline (Dox)-inducible ras oncogene, withdrawal of Dox (thus ras oncogene down-regulation) results in regression by marked apoptosis of primary and explanted tumor cells. The ras oncogene-dependency of melanoma cell maintenance in this model could be explained by the existence of a melanoma cell-specific survival pathway positively regulated by the MAPK cascade that can be constitutively activated by ras oncogene activation or upstream receptor tyrosine kinase activation Lewis, T. S. et al., Adv Canc Res 74:49-139 (1998); Roussel et al., supra).

EXAMPLE VI

Anthrax Lethal Factor and PD98059 Act on Various other Tumors

Unexpectedly, among the breast carcinoma cell lines in NCI-ADS, two related cell lines MDA-MB-435 and MDA-N were as sensitive as melanoma cell lines to the growth inhibition rendered by LF or PD98059. (See Table 5.) However, recent cDNA microarray analysis of approximately 8,000 different genes revealed that these cell lines were derived from a single patient with breast cancer (Cailleau, R. et al., In Vitro 14:911-915 (1978)) and exhibited the gene expression profile more characteristic of melanoma cells, suggesting that these cells may have originated from a melanoma rather than the mammary adenocarcinoma (Ross et al., supra).

These findings not only provide an explanation for the enhanced sensitivity of these tumor cells to LF or PD98059, but also corroborate the present inventors' finding that human melanoma cells are specifically sensitive to inhibition of the MAPK pathway.

The incidence of malignant melanoma is increasing dramatically in all parts of the world (Parker, S. et al., *CA Cancer J Clin* 47:5-27 (1997)). Despite improved diagnosis and characterization, long-term survival from the advanced disease has not improved. The present findings that inhibition of MAPK signaling specifically triggers an apoptotic response in human melanoma cells, but not in normal melanocytes or in other cell types, makes this a novel selective therapeutic strategy for systematic treatment of malignant melanomas.

TABLE 5

Sensitivity of Human Tumor Cell Lines of NCI-ADS Cancer Panels to LF and PD98059*

| Treatment | Melanoma panel | Other tumor panel† |
|---|---|---|
| LF | 0.63 ng/ml | 540 ng/ml |
| PD98059 | $1.61 \times 10^{-5}$ M | $5.04 \times 10^{-5}$ M |

*Sensitivity is determined using a sulforhodamine-B assay after 2-day incubation with the inhibitors and is indicated as the concentration of inhibitor yielding 50% inhibition of cell growth (Monks et al, J. Natl Cancer Inst, 83: 757-766).

†Central nervous system. Non-small cell lung, colon, CNS, ovarian, renal, prostate, breast cancer panels and leukemia panel

EXAMPLE VII

MAPK Pathway Inhibition In Vivo Inhibits Tumor Growth

To evaluate the effects of MAPK pathway inhibition on growth of melanoma in vivo, M14-MEL or SK-MEL-28 cells were xenografted s.c. into female athymic nude mice (NCR nu/nu mice about 8 weeks old). Results are shown in FIGS. 14-18. When the tumors became established (mass of ~95 mg), treatment with LF was initiated (Day 13). The test group (n=7) was treated daily first with 2 μg of LF (+6 μg of PA)/mouse for 4 days (Day 13-16) and then with 4 μg of LF (+6 μg PA)/mouse for another 9 days (Day 17-25). The control group (n=6) was treated with PA alone (6 μg/mouse) daily during the same period (Day 13-25).

Treatment with LF significantly attenuated the growth of M14-MEL tumors in vivo. Furthermore, a dose effect was observed: growth inhibition was greater with 4 μg of LF than with 2 μg of LF and the tumors grew at a faster rate when treatment was stopped. Tumor growth was not affected by treatment with PA alone. Tumor size varied more in animals treated with PA alone than in those treated with LF. The inhibitory effects on tumors were also manifest as a difference in tumor depth.

Histological examination (not shown) of the tumors further revealed qualitative differences of LF-treatment compared to the control (PA alone). Tumors in PA-treated subjects showed signs of hemorrhage, while tumors treated with LF were occupied with a central white mass. To examine cellular structure and apoptosis, tumor sections were stained with H&E and by TUNEL, respectively. Cellular organization was absent in the white mass in tumors of the LF-treated group and these exhibited strong TUNEL positivity, especially at the junction between the white mass and light-brown layer. Higher magnification revealed that nuclei were severely fragmented, a typical sign of apoptosis. Thus, it was concluded that after LF treatment, tumors were filled with dead and apoptotic cells (white mass), and this region was surrounded by live tumor cells (light-brown layer). In PA-treated tumors, the hemorrhagic zone scored positive for TUNEL because of the endogenous peroxidase activity of the red blood cells. Importantly, TUNEL-positive apoptotic cells were not seen.

LF prevented M14-MEL tumors from growing (40% overall reduction in tumor size at day 31, FIG. 16A). When the LF treatment was halted for M14-MEL tumors, one tumor continued to regress, while the majority slowly resumed growth (FIG. 16A). LF had a much more dramatic effect on SK-MEL-28 xenografts (FIG. 16B). All tumors in this series regressed completely during LF treatment, and the animals remained tumor-free for up to 5 weeks (FIG. 16B). PA alone had no effect on tumor growth in either study. Unexpectedly, SK-MEL-28 melanoma cells were more sensitive to LF in vivo than in vitro (Table 4) suggesting a stronger requirement of the MEK/MAPK signaling for melanoma cell survival in vivo. The variation in response of M14-MEL and SK-MEL-28 tumors to LF may be due to the differences in in vivo growth rate (FIG. 16) and in tumor size at initial treatment. Histological characterization revealed qualitative differences between the LF- and PA-treated tumors.

FIG. 18 also shows the effect of LF treatment of SK-MEL-28 by direct intratumoral injection. When tumor growth was established (volume of ~310 $mm^3$ on day 27 after implantation), tumors were treated with 6 μg PA+2 μg LF/mouse (PA+LF) or 6 μg PA/mouse as controls). Five doses were given at 2-day intervals over days 27-35 and then an additional dose was given on day 38. The PA+LF-treated tumors remained in complete regression for at least 71 days. PA alone had no effect on tumor growth. Standard deviations (SD) of PA-treated tumors, ranged from 48 mm³ (day 27) to 250 mm³ (day52); SD's of PA+LF-treated tumors ranged from 56 mm³ (day 27) to 32 mm³ (day 35).

Histological characterization revealed qualitative differences between the LF- and PA-treated tumors. The following description is of a comparison of the effects of LF on two melanomas (see also discussion above for M14-MEL results). Tumors of the control groups treated with PA alone showed hemorrhage and necrosis (FIGS. 17A, 17B, and 17J, 17K). The area around necrotic foci (FIG. 17C) and sporadic tumor cells (FIG. 17L) stained positive for TUNEL. In contrast, the LF-treated M14-MEL tumors were largely void of organized cellular structures and were packed with fragmented nuclei, which stained intensely for TUNEL (FIG. 17D-17I), indicating apoptotic cell death. Some surviving tumor cells, however, were detected at the periphery of the M14-MEL tumor (FIG. 17D-17F). In SK-MEL-28 tumors, all tumor cells remaining were strongly stained (FIG. 17M-17R). Moreover, melanin deposits were evident throughout the LF-treated tumors (insets in FIGS. 17E, 17H, 17N and 17Q), consistent induction of melanin production by LF. LF had no apparent side effects during and following treatment.

These results demonstrated that the strategy of inhibiting the MAPK pathway triggered cell death by apoptosis in melanomas growing in vivo.

Figure 19:
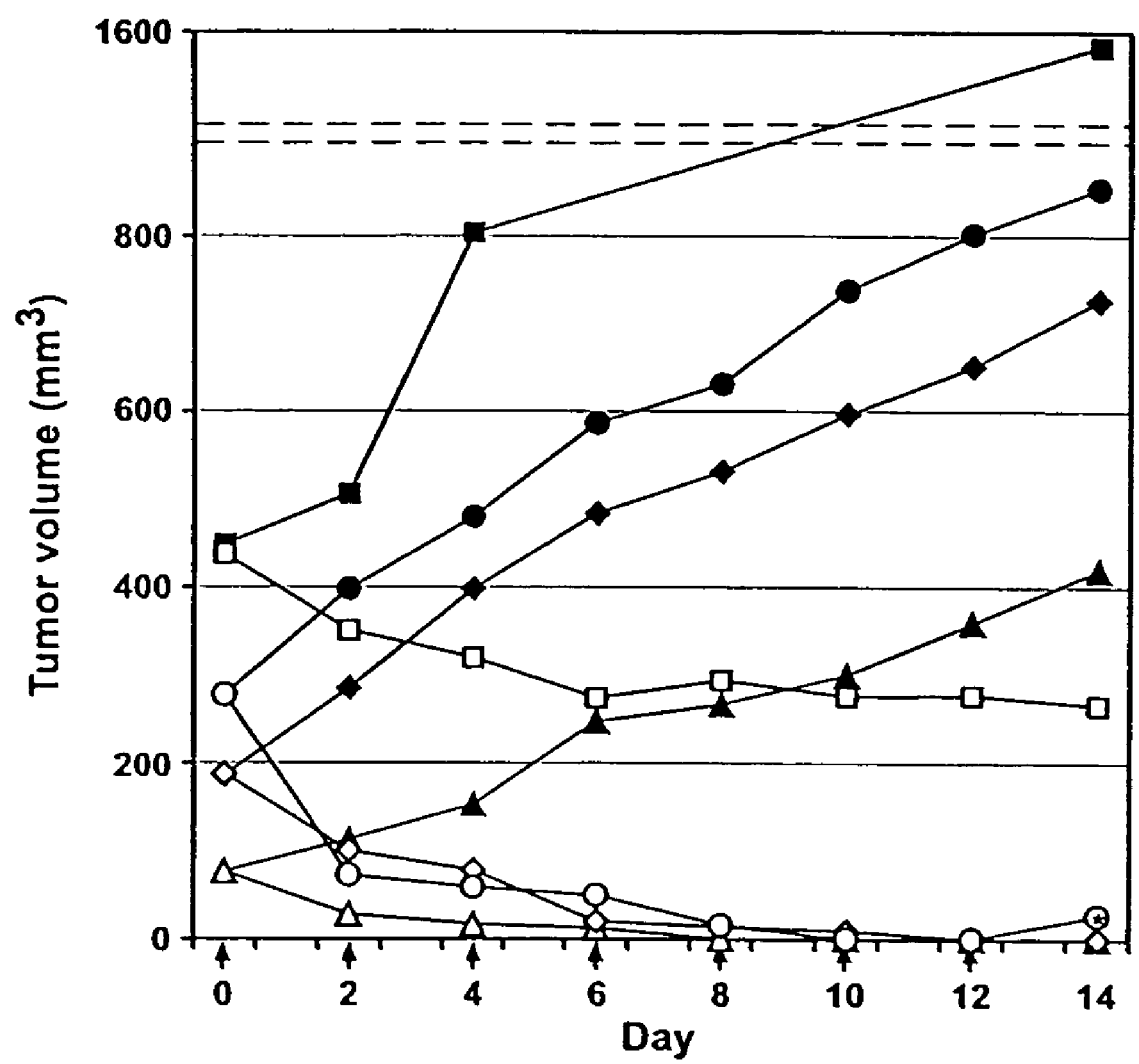
FIG. 19 is a graph showing an inverse relationship between the tumor size and the antitumor effects of LF treatment. When M14-MEL melanoma xenograft tumor size reached various approximate sizes: 76 $mm^3$ (▲Δ, n=4 each), 187 $mm^3$ (♦◊, n=4), 278 $mm^3$ (○●, n=4), or 443 $mm^3$ (■□, n=7), treatment by direct intratumoral injection was initiated. Treatment involved 7 doses (↑) at 2-day intervals of 6 μg PA+2 μg LF/mouse (open symbols) or 6 μg PA/mouse as controls (solid symbols). Two of the 278-mm³ tumors (* inside ○) started to regrow after cessation of treatment. At the end of the treatment interval (day 14), "control" tumors treated with PA showed significant variation in volume (SD from 109 to 263 $mm^3$), whereas, only tumors of the 443-$mm^3$ group survived PA+LF treatment and were of various sizes (SD from 23 to 131 $mm^3$).

Results in FIG. 19 show an inverse relationship between the tumor size and the antitumor effects of LF treatment. The PA+LF treatment regimen caused complete regression of the three groups of tumors that were initially smaller (76, 187, and 278-mm³) and approximately 40% overall reduction in larger tumors (initial size ~443-mm³) PA alone had no effect on tumor growth. At the end of the treatment interval (day 14), "control" tumors treated with PA showed significant variation in-volume (SD from 109 to 263 mm³), whereas, only tumors of the 443-mm³ group survived PA+LF treatment varied in volumes (SD from 23 to 131 mm³).

EXAMPLE VIII

Figure 21:
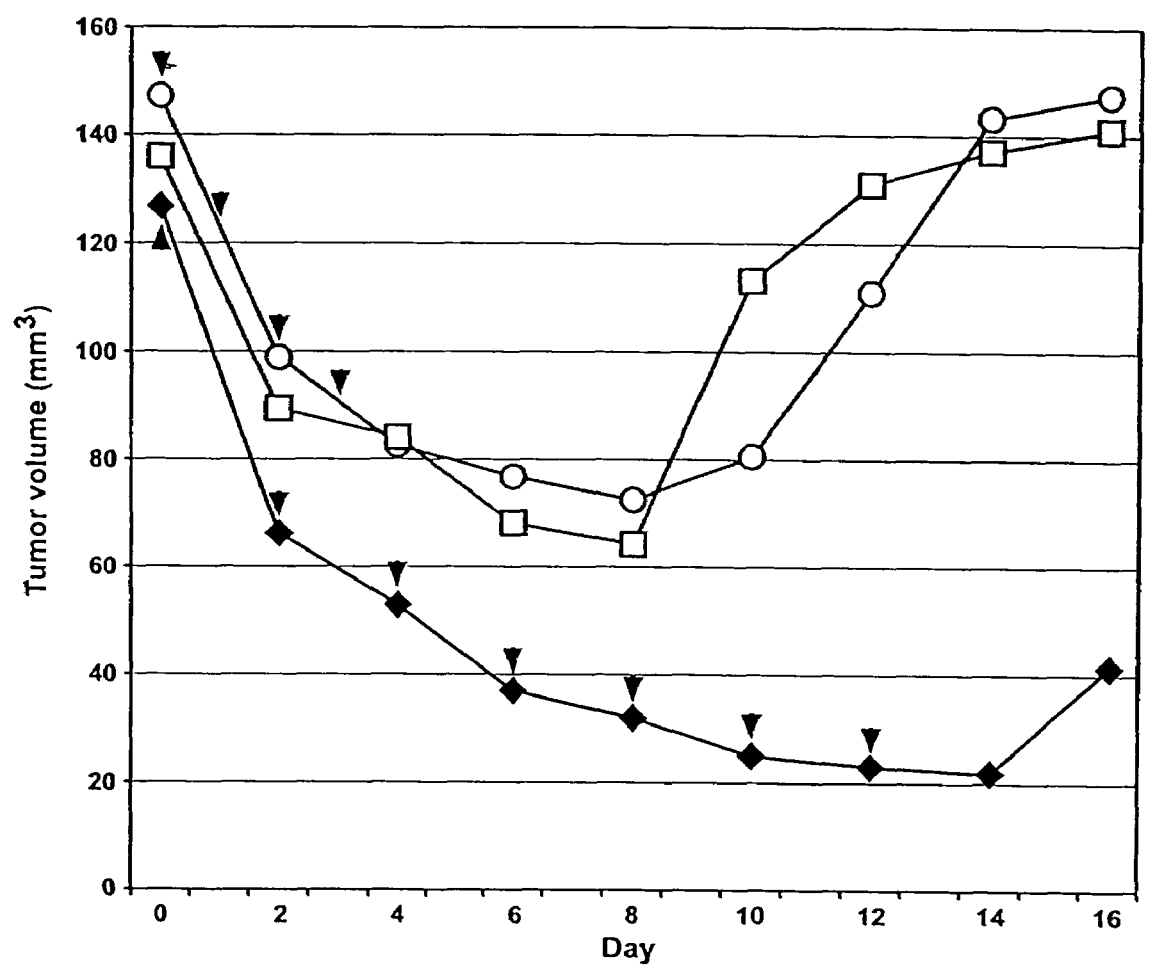
FIG. 21 shows the effects of LF administered IV treatment on MALME-3M melanoma xenograft tumor growth. Each curve represents one mouse. Three nude mice bearing MALME-3M tumors were injected IV first with 2 μg LF/mouse followed one hour later by 20 μg PA/mouse.

LF Administered Intravenously Inhibits Growth of MALME-3M Melanoma Xenograft Three nude mice bearing MALME-3M tumors were injected IV in the lateral tail vein first with 2 µg LF/mouse followed by 20 µg PA/mouse one hour later. Results are shown in FIG. 21 Treatment was either daily (○ and □) or at 2-day intervals (♦). For the daily treatment animal, a total of 4 doses was given; for the 2-day interval schedule, a total of 7 doses were given (arrowheads). Both these systemic treatment protocols resulted in tumor regression.

The IV treatment regimen selected for further studies was: IV injection first with 2 µg LF/mouse and followed one hour later by 20 µg PA/mouse; this combination treatment was administered using 2-day intervals. Based on the results in FIG. 21, the following regimen is used and the following outcomes are expected:

Tumors: Subcutaneous MALME-3M xenograft tumors in one dorsolateral flank (~100 mm³).

Treatment Protocol: Intravenous injection (tail vein) of 50 µl volumes

TABLE 6

Treatment schedule at 2-day intervals

| Group | n | First IV injection | Interval | Second IV injection | Expected Results |
|---|---|---|---|---|---|
| A | ≧5 | — | — | 20 µg PA/mouse | Tumor Growth |
| B | ≧5 | 2 µg LF/mouse | 15 min | 20 µg PA/mouse | Regression |
| C | ≧5 | 2 µg LF/mouse | 1 hour | 20 µg PA/mouse | Regression |
| D | ≧5 | 10 µg LF/mouse | 1 hour | 20 µg PA/mouse | Regression |

EXAMPLE IX

Systemic Effect of LF Treatment on Growth of MALME-3M Melanomas

Figures 20A, 20B:
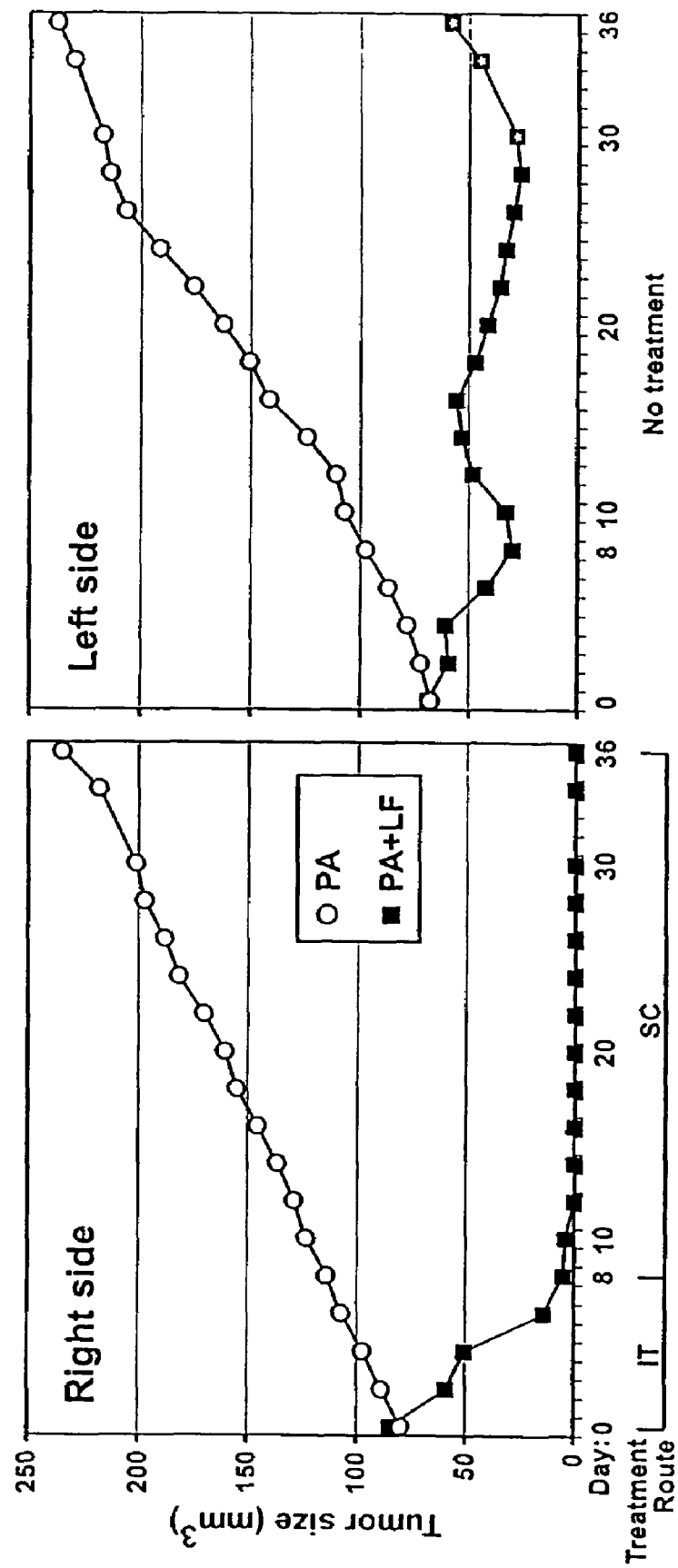
FIGS. 20A and 20B are graphs showing the systemic effect of LF treatment on the growth of MALME-3M melanoma tumors. MALME-3M cells were injected subcutaneously (s.c.) into both right and left dorsal upper flank areas of athymic nude mice. When tumor growth was established, the animals were randomized (n=5) based on the size of the left-side tumor (~70 mm$^3$). Treatment began by direct intratumoral (IT) injection at 2 day intervals only into right-side ("ipsilateral") tumors of 10 μg PA+2 μg LF/mouse (PA+LF, ■) or 10 μg PA/mouse for controls (PA, ○). Contralateral (left-side) tumors were left untreated. When ipsilateral tumors shrunk to a size that could not be visualized (in the PA+LF-treated group), at around day 10, the treatment route was changed to ipsilateral s.c. injection approximately where the tumors had been. Each point is the mean of the group; analysis of each individual showed that two of the contralateral tumors continuously regressed, whereas one grew back and the remaining two showed signs of regrowth after the 16$^{th}$ treatment.

MALME-3M cells were injected subcutaneously (s.c.) into both right and left dorsal upper flank areas of athymic nude mice. When tumor growth was established, the animals were randomized (n=S) based on the size of the left-side tumor (~70 mm³). Treatment began by direct intratumoral (IT) injection at 2 day intervals only into right-side ("ipsilateral") tumors of 10 µg PA+2 µg LF/mouse or 10 µg PA/mouse for controls. Contralateral (left-side) tumors were left untreated. When ipsilateral tumors shrunk to a size that could not be visualized (in the PA+LF-treated group), at around day 10, the treatment route was changed to ipsilateral s.c. injection approximately where the tumors had been. Results are shown in FIGS. 20A and 20B.

Ipsilateral MALME-3M tumors directly treated with PA+LF completely regressed after 6 doses. More importantly, the contralateral tumors also began to regress immediately. At the time the treatment route changed, contralateral tumors showed signs of regrowth but with continued treatment, began to regress again, whereas ipsilateral tumors never recurred. While each point is the mean of the group, analysis of each individual showed that two of the contralateral tumors continuously regressed, whereas one tumor grew back and the remaining two showed signs of regrowth after the 16$^{th}$ treatment. Treatment with PA alone had no effect on tumor growth either ipsi- or contralaterally. These results indicate that the antitumor effects of intratumoral/s.c. LF treatment became systemic (presumably through distribution via blood vessels, lymphatic networks, or both). A total of 19 LF doses were tolerated without any observable adverse effects on general health and behavior of the animals.

EXAMPLE X

Anti Tumor Effects of Infused Melanoma Cytotoxic Composition in Human Patients All patients treated have histologically confirmed melanoma and have failed conventional therapy. Patients may be diagnosed as having any stage of metastatic disease involving any organ system. Staging describes both tumor and host, including organ of origin of the tumor, histologic type, histologic grade, extent of tumor size, site of metastases and functional status of the patient. A general classification includes the known ranges of Stage 1 (localized disease) to Stage 4 (widespread metastases). Patient history is obtained and physical examination performed along with conventional tests of cardiovascular and pulmonary function and appropriate radiologic procedures. Histopathology is obtained to verify malignant disease.

Treatment Procedure

Doses of the test composition are determined as described above using, inter alia, appropriate animal models of melanoma.

Two general classes of therapeutic compositions, described above, are administered:
(1) Proteins MEK-proteases or functional derivatives;
(2) Small Molecule MEK inhibitors A treatment consists of injecting the patient with 1, 100 or 1000 μg of protein or polypeptide intravenously in 200 ml of normal saline over a one-hour period. Treatments are given 3×/week for a total of 12 treatments. Patients with stable or regressing disease are treated beyond the 12th treatment. Treatment is given on either an outpatient or inpatient basis as needed.

Patient Evaluation

Assessment of response of the tumor to the therapy is made once per week during therapy and 30 days thereafter. Depending on the response to treatment, side effects, and the health status of the patient, treatment is terminated or prolonged from the standard protocol given above. Tumor response criteria are those established by the International Union Against Cancer and are listed below.

| RESPONSE | DEFINITION |
| --- | --- |
| Complete remission (CR) | Disappearance of all evidence of disease |
| Partial remission (PR) | ≧50% decrease in the product of the two greatest perpendicular tumor diameters; no new lesions |
| Less than partial remission (<PR) | 25%-50% decrease in tumor size, stable for at least 1 month |
| Stable disease | <25% reduction in tumor size; no progression or new lesions |
| Progression | ≧25% increase in size of any one measured lesion or appearance of new lesions despite stabilization or remission of disease in other measured sites |

The efficacy of the therapy in a patient population is evaluated using conventional statistical methods, including, for example, the Chi Square test or Fisher's exact test. Long-term changes in and short term changes in measurements can be evaluated separately.

Results

One hundred and fifty patients are treated. The results are summarized below. Positive tumor responses (at least partial remission) are observed in over 80% of the patients as follows:

| Response | % |
| --- | --- |
| PR | 66% |
| <PR | 20% |
| PR + <PR | 86% |

Toxicity

The incidence of side effects are between 10% and <1% of total treatments and include (in decreasing frequency): chills, fever; pain, nausea, respiratory, headache, tachycardia, vomiting, hypertension, hypotension, joint pain, rash, flushing, diarrhea, itching/hives, bloody nose, dizziness, cramps, fatigue, feeling faint, twitching, blurred vision, gastritis, redness on hand. Other minor changes observed are clinically insignificant.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A method of killing melanoma cells comprising contacting melanoma cells for an effective time with an effective amount of *Bacillus anthracis* lethal factor (LF), thereby killing the melanoma cells.

2. The method of claim 1, wherein said contacting is in vivo.

3. The method of claim 2, wherein said killing results in measurable regression of a melanoma tumor or attenuation of melanoma tumor growth.

4. A method of inducing an antitumor response in a mammal having melanoma, comprising administering to a mammal having melanoma an effective amount of *Bacillus anthracis* lethal factor, wherein administration of the *Bacillus anthracis* lethal factor results in a cytotoxic effect on melanoma cells, thereby inducing an antitumor response.

5. The method of claim 4 wherein the antitumor response is:
   (a) a partial antitumor response characterized by
      (i) at least 50% decrease in the sum of maximal perpendicular diameters of all measurable lesions;
      (ii) no evidence of new lesions, and
      (iii) no progression of any preexisting lesions, or
   (b) a complete antitumor response characterized by the disappearance of all evidence of melanoma disease for at least one month.

6. The method of claim 5 wherein said antitumor response is a partial antitumor response.

7. The method of claim 5 wherein said mammal is a human.

8. A method of inhibiting the primary growth of melanoma in a mammal which has melanoma, comprising administering to said mammal an effective amount of *Bacillus anthracis* lethal factor, thereby inhibiting said primary growth of said melanoma.

9. The method of claim 8 wherein said mammal is a human.

* * * * *

UNITED STATES PATENT AND TRADEMARK OFFICE
CERTIFICATE OF CORRECTION

PATENT NO. : 7,612,035 B2                                            Page 1 of 8
APPLICATION NO. : 11/155691
DATED : November 3, 2009
INVENTOR(S) : Han-Mo Koo et al.

It is certified that error appears in the above-identified patent and that said Letters Patent is hereby corrected as shown below:

Title page, item (*) Notice: Subject to any disclaimer, the term of this patent is extended or adjusted under 35 U.S.C. 154(b) by 323 days.

Delete the phrase "by 323 days" and insert -- by 818 days --.

Col. 1, line 56

"them,." should be -- them, --;

Col. 1, line 67

"711-(1998)" should be -- 711 (1998) --;

Col. 2, line 31

"applicant" should be -- applicants --;

Col. 3, line 3

"lesions;" should be -- lesions, --;

Col. 3, line 54

"a. 1:1" should be -- a 1:1 --;

Col. 3, line 66

After "because" delete "the";

Col. 4, line 33

"lesions;" should be -- lesions, --;

Signed and Sealed this

Twenty-fourth Day of August, 2010

David J. Kappos
*Director of the United States Patent and Trademark Office*

Col. 4, line 67

After "indicated" insert -- . --;

Col. 5, line 16

"antibodies)" should be -- antibodies, --;

Col. 5, line 33

"Fig. 4" should be -- Fig. 4. --;

Col. 5, line 36

"cells" should be -- cells. --;

Col. 5, line 41

"11A-1D" should be -- 11A-11D --;

Col. 5, line 49

"Figs. 11C and 11C" should be -- Figs. 11C and 11D --;

Col. 5, line 59

After "treated" delete "either";

Col. 6, line 8

"inset )" should be -- inset) --;

Col. 6, line 16

"SK- MEL-28" should be -- SK-MEL-28 --;

Col. 6, line 19

"(PA, 0)" should be -- (PA, O) --;

Col. 6, line 24

"mm3" should be -- mm$^3$ --;

Col. 6, line 25

"x axis" should be -- x-axis --;

Col. 6, line 26

" ⇓ " should be -- ⬇ --;

Col. 6, line 29

"ofthe" should be -- of the --;

Col. 6, line 32

After "examined" delete ".";

Col. 6, line 37

"ε" should be -- C --;

Col. 6, line 49

"⇓" should be -- ↓ --;

Col. 6, lines 50-51

"mM3 (day52); SD's" should be -- $mm^3$ (day 52); SDs --;

Col. 7, line 20

"IV" should be -- i.v. --;

Col. 7, line 26

"was" should be -- were --;

Col. 7, line 55

"repeated. cycles" should be -- repeated cycles --;

Col. 7, line 60

"yours" should be -- hours --;

Col. 8, line 39

"etc.)." should be -- etc. --;

Col. 8, line 46

"thereof;" should be -- thereof, --;

Col. 8, line 59

"4098-4094" should be -- 4089 - 4094 --;

Col. 9, lines 5-6

After "exerts" delete "is";

Col. 9, lines 17-18

After "which" (first occurrence) delete "is";

Col. 9, line 32

"animals" should be -- animal --;

Col. 10, line 13

After "(Cys)" insert -- ; --;

Col. 10, line 64

After "molecule" remove -- is --;

Col. 10, line 65

After "may" insert -- be --;

Col. 13, line 13

"Proteins" should be -- Protein --;

Col. 13, line 48

After "amplify" delete "a";

Col. 14, line 32

"fillers binders" should be -- fillers, binders --;

Col. 14, line 62

"Treatments" should be -- Treatment --;

Col. 15, line 15

After "administration" delete "of";

Col. 15, line 43

"iv" should be -- i.v. --;

Col. 15, line 49

"iv" should be -- i.v. --;

Col. 15, line 63

After "In" delete "a";

Col. 16, line 10

"nonsprayable" should be -- non-sprayable --;

Col. 16, line 7

"I." should be -- 1. --;

Col. 17, line 54

"are" should be -- is --;

Col. 19, line 1

"are-computed the factors" should be -- are computed using the factors --;

Col. 19, lines 9 and 11

"use" should be -- used --;

Col. 19, line 34

"(C57BL16" should be -- (C57B/6 --;

Col. 19, line 48

"or" should be -- of --;

Col. 20, line 2

"no takes" should be -- no-takes --;

Col. 20, line 13

"B 16" should be -- B16 --;

Col. 20, line 17

"Mice sacrificed" should be -- Mice are sacrificed --;

Col. 20, line 59

"((Boyd" should be -- (Boyd --;

Col. 20, line 61

"Lippinicott" should be -- Lippincott --;

Col. 21, line 3

After "Compounds" delete "of";

Col. 22, lines 32, 36, 38

"2-1", "6-6" and "8-2" should be -- 2.1 --, -- 6.6 -- and -- 8.2 --;

Col. 23, line 4

After "of" delete "-";

Col. 23, line 19

"T$_I$" should be -- T$_1$ --;

Col. 23, line 39

"loglo" should be -- log$_{10}$ --;

Col. 23, line 59

"defined-as" should be -- defined as --;

Col. 23, line 60

"the, tumor" should be -- the tumor --;

Col. 24, line 33

"model as one" should be -- model is one --;

Col. 24, line 41

"(A)" should be -- (Δ) --;

Col. 25, line 5

"are-designated" should be -- are designated --;

Col. 25, line 28

"tumors models" should be -- tumor models --;

Col. 25, line 47

"(1995)." should be -- (1995)). --;

Col. 25, line 56

"activity" should be -- activity --;

Col. 26, line 10

"016" should be -- 0/6 --;

Col. 26, line 11

"17 21" should be -- 17, 21 --;

Col. 27, line 37

"1993))." should be -- 1993). --;

Col. 27, line 47

"iv" should be -- i.v. --;

Col. 27, line 60

"66: 131-1f58" should be -- 66(2): 151-158 --;

Col. 27, line 61

"reference) described" should be -- reference described --;

Col. 27, line 63

"line. C8161" should be -- line C8161 --;

Col. 28, line 9

"neo C8161" should be -- neo⁻C8161 --;

Col. 28, line 17

"hematogenouso" should be -- hematogenous --;

Col. 28, line 30

"(1989))." should be -- (1989). --;

Col. 28, line 41

"hygromycin)." should be -- hygromycin)). --;

Col. 29, line 24

"pUHDI72-Ineo" should be -- pUHD172-1neo --;

Col. 29, line 27

"tet" should read -- Tet --;

Col. 29, line 32

"(1983)." should be -- (1983) and --;

Col. 29, line 33

"et al. (Nature . . . (1999))" should be -- et al. Nature . . . (1999) --;

CERTIFICATE OF CORRECTION (continued)
U.S. Pat. No. 7,612,035 B2

Col. 29, line 48

"cell" should be -- cells --;

Col. 29, line 58

"H-Ras$v^{V12G}$" should be -- H-Ras$^{V12G}$ --;

Col. 29, line 60

"tet-operons" should be -- Tet-operons --;

Col. 29, line 66

"INK4$^{-/-}$" should be -- INK4a$^{-/-}$ --;

Col. 31, line 49

"mass of 95 mg" should be -- mass of ~95 mg --;

Col. 32, line 5

"Detection, POD" should be -- Detection," POD --;

Col. 32, line 8

"light-blue" should be -- light blue. --;

Col. 32, lines 21 and 23

"medium Dudley . . . (1995)) Again," should be -- medium (Dudley . . . (1995)). Again, --;

Col. 32, lines 43 and 44

"1-24 1998) . . . supra." should be -- 1-24 (1998) . . . supra). --;

Col. 32, line 65

"(Fig. 3A-3G)" should be -- (Figs. 3A-3G) --;

Col. 34, line 52

"PD98059" should be -- PD98059. --;

Col. 35, line 20

"activation Lewis" should be -- activation (Lewis --;

Col. 37, line 2

"(day52)" should be -- (day 52) --;

Col. 37, lines 16, 19 and 20

"(Fig." should be -- (Figs. --;

Col. 37, line 37

"in-volume" should be -- in volume --;

Col. 37, line 51

"Fig 21 Treatment" should be -- Fig. 21. Treatment --;

Col. 37, line 53

"was" should be -- were --;

Col. 37, line 66

"volumes" should be -- volumes. --;

Col. 38, line 24

"(n=S)" should be -- (n=5) --;

Col. 39, line 7

"inhibitors" should be -- inhibitors. --;

Col. 39, line 42

"short term" should be -- short-term --.

UNITED STATES PATENT AND TRADEMARK OFFICE
CERTIFICATE OF CORRECTION

PATENT NO.         : 7,612,035 B2
APPLICATION NO.    : 11/155691
DATED              : November 3, 2009
INVENTOR(S)        : Han-Mo Koo et al.

Page 1 of 8

It is certified that error appears in the above-identified patent and that said Letters Patent is hereby corrected as shown below:

On the Title Page:

The first or solo Notice should read --

Subject to any disclaimer, the term of this patent is extended or adjusted under 35 U.S.C. 154(b) by 818 days.

Col. 1, line 56

"them,." should be -- them, --;

Col. 1, line 67

"711-(1998)" should be -- 711 (1998) --;

Col. 2, line 31

"applicant" should be -- applicants --;

Col. 3, line 3

"lesions;" should be -- lesions, --;

Col. 3, line 54

"a. 1:1" should be -- a 1:1 --;

Col. 3, line 66

After "because" delete "the";

Col. 4, line 33

"lesions;" should be -- lesions, --;

This certificate supersedes the Certificate of Correction issued August 24, 2010.

Signed and Sealed this

Twenty-eighth Day of September, 2010

David J. Kappos
*Director of the United States Patent and Trademark Office*

Col. 4, line 67

After "indicated" insert -- . --;

Col. 5, line 16

"antibodies)" should be -- antibodies, --;

Col. 5, line 33

"Fig. 4" should be -- Fig. 4. --;

Col. 5, line 36

"cells" should be -- cells. --;

Col. 5, line 41

"11A-1D" should be -- 11A-11D --;

Col. 5, line 49

"Figs. 11C and 11C" should be -- Figs. 11C and 11D --;

Col. 5, line 59

After "treated" delete "either";

Col. 6, line 8

"inset )" should be -- inset) --;

Col. 6, line 16

"SK- MEL-28" should be -- SK-MEL-28 --;

Col. 6, line 19

"(PA, 0)" should be -- (PA, O) --;

Col. 6, line 24

"mm3" should be -- $mm^3$ --;

Col. 6, line 25

"x axis" should be -- x-axis --;

Col. 6, line 26

" ⇓ " should be -- ⬇ --;

Col. 6, line 29

"ofthe" should be -- of the --;

Col. 6, line 32

After "examined" delete ".";

Col. 6, line 37

"ε" should be -- C --;

Col. 6, line 49

"⇓" should be -- ↓ --;

Col. 6, lines 50-51

"mM3 (day52); SD's" should be -- mm$^3$ (day 52); SDs --;

Col. 7, line 20

"IV" should be -- i.v. --;

Col. 7, line 26

"was" should be -- were --;

Col. 7, line 55

"repeated. cycles" should be -- repeated cycles --;

Col. 7, line 60

"yours" should be -- hours --;

Col. 8, line 39

"etc.)." should be -- etc. --;

Col. 8, line 46

"thereof;" should be -- thereof, --;

Col. 8, line 59

"4098-4094" should be -- 4089 - 4094 --;

Col. 9, lines 5-6

After "exerts" delete "is";

Col. 9, lines 17-18

After "which" (first occurrence) delete "is";

Col. 9, line 32

"animals" should be -- animal --;

Col. 10, line 13

After "(Cys)" insert -- ; --;

Col. 10, line 64

After "molecule" remove -- is --;

Col. 10, line 65

After "may" insert -- be --;

Col. 13, line 13

"Proteins" should be -- Protein --;

Col. 13, line 48

After "amplify" delete "a";

Col. 14, line 32

"fillers binders" should be -- fillers, binders --;

Col. 14, line 62

"Treatments" should be -- Treatment --;

Col. 15, line 15

After "administration" delete "of";

Col. 15, line 43

"iv" should be -- i.v. --;

Col. 15, line 49

"iv" should be -- i.v. --;

Col. 15, line 63

After "In" delete "a";

Col. 16, line 10

"nonsprayable" should be -- non-sprayable --;

Col. 16, line 57

"I." should be -- 1. --;

Col. 17, line 54

"are" should be -- is --;

Col. 19, line 1

"are-computed the factors" should be -- are computed using the factors --;

Col. 19, lines 9 and 11

"use" should be -- used --;

Col. 19, line 34

"(C57BL16" should be -- (C57B/6 --;

Col. 19, line 48

"or" should be -- of --;

Col. 20, line 2

"no takes" should be -- no-takes --;

Col. 20, line 13

"B 16" should be -- B16 --;

Col. 20, line 17

"Mice sacrificed" should be -- Mice are sacrificed --;

Col. 20, line 59

"((Boyd" should be -- (Boyd --;

Col. 20, line 61

"Lippinicott" should be -- Lippincott --;

Col. 21, line 3

After "Compounds" delete "of";

Col. 22, lines 32, 36, 38

"2-1", "6-6" and "8-2" should be -- 2.1 --, -- 6.6 -- and -- 8.2 --;

Col. 23, line 4

After "of" delete "-";

Col. 23, line 19

"$T_I$" should be -- $T_1$ --;

Col. 23, line 39

"loglo" should be -- $log_{10}$ --;

Col. 23, line 59

"defined-as" should be -- defined as --;

Col. 23, line 60

"the, tumor" should be -- the tumor --;

Col. 24, line 33

"model as one" should be -- model is one --;

Col. 24, line 41

"(A)" should be -- (Δ) --;

Col. 25, line 5

"are-designated" should be -- are designated --;

Col. 25, line 28

"tumors models" should be -- tumor models --;

Col. 25, line 47

"(1995)." should be -- (1995)). --;

Col. 25, line 56

"activity" should be -- activity --;

Col. 26, line 10

"016" should be -- 0/6 --;

Col. 26, line 11

"17 21" should be -- 17, 21 --;

Col. 27, line 37

"1993))." should be -- 1993). --;

Col. 27, line 47

"iv" should be -- i.v. --;

Col. 27, line 60

"66: 131-1f58" should be -- 66(2): 151-158 --;

Col. 27, line 61

"reference) described" should be -- reference described --;

Col. 27, line 63

"line. C8161" should be -- line C8161 --;

Col. 28, line 9

"neo C8161" should be -- neo⁻C8161 --;

Col. 28, line 17

"hematogenouso" should be -- hematogenous --;

Col. 28, line 30

"(1989))." should be -- (1989). --;

Col. 28, line 41

"hygromycin)." should be -- hygromycin)). --;

Col. 29, line 24

"pUHDI72-Ineo" should be -- pUHD172-1neo --;

Col. 29, line 27

"tet" should read -- Tet --;

Col. 29, line 32

"(1983)." should be -- (1983) and --;

Col. 29, line 33

"et al. (Nature . . . (1999))" should be -- et al. Nature . . . (1999) --;

Col. 29, line 48

"cell" should be -- cells --;

Col. 29, line 58

"H-Rasv$^{V12G}$" should be -- H-Ras$^{V12G}$ --;

Col. 29, line 60

"tet-operons" should be -- Tet-operons --;

Col. 29, line 66

"INK4$^{-/-}$" should be -- INK4a$^{-/-}$ --;

Col. 31, line 49

"mass of 95 mg" should be -- mass of ~95 mg --;

Col. 32, line 5

"Detection, POD" should be -- Detection," POD --;

Col. 32, line 8

"light-blue" should be -- light blue. --;

Col. 32, lines 21 and 23

"medium Dudley . . . (1995)) Again," should be -- medium (Dudley . . . (1995)). Again, --;

Col. 32, lines 43 and 44

"1-24 1998) . . . supra." should be -- 1-24 (1998) . . . supra). --;

Col. 32, line 65

"(Fig. 3A-3G)" should be -- (Figs. 3A-3G) --;

Col. 34, line 52

"PD98059" should be -- PD98059. --;

Col. 35, line 20

"activation Lewis" should be -- activation (Lewis --;

Col. 37, line 2

"(day52)" should be -- (day 52) --;

Col. 37, lines 16, 19 and 20

"(Fig." should be -- (Figs. --;

Col. 37, line 37

"in-volume" should be -- in volume --;

Col. 37, line 51

"Fig 21 Treatment" should be -- Fig. 21. Treatment --;

Col. 37, line 53

"was" should be -- were --;

Col. 37, line 66

"volumes" should be -- volumes. --;

Col. 38, line 24

"(n=S)" should be -- (n=5) --;

Col. 39, line 7

"inhibitors" should be -- inhibitors. --;

Col. 39, line 42

"short term" should be -- short-term --.